(12) United States Patent
Kramarov et al.

(10) Patent No.: US 6,630,319 B1
(45) Date of Patent: Oct. 7, 2003

(54) THERMOSTABLE DNA POLYMERASE

(75) Inventors: Vladimir Matveevich Kramarov, Moscow (RU); Konstantin Borisovich Ignatov, Moscow (RU); James Peter Hallinan, London (GB)

(73) Assignee: Bioline Limited, London (GB)

( * ) Notice: Subject to any disclaimer, the term of this patent is extended or adjusted under 35 U.S.C. 154(b) by 0 days.

(21) Appl. No.: 09/379,530

(22) Filed: Aug. 24, 1999

(30) Foreign Application Priority Data

Aug. 24, 1998 (GB) .............................................. 9818432

(51) Int. Cl.[7] .......................... C12N 9/12; C07H 21/04; C12Q 1/48
(52) U.S. Cl. .................. 435/15; 435/183; 435/91.1; 435/194; 435/6; 536/23.1; 536/23.2; 536/23.4; 536/23.7; 530/350; 424/94.5
(58) Field of Search .................. 435/194, 183, 435/15, 6, 91.1; 530/350; 424/94.5; 536/23.7, 23.1, 23.2, 23.4

(56) References Cited

U.S. PATENT DOCUMENTS 5,466,591 A    11/1995  Abramson et al. ........... 435/194
6,228,628 B1 *  5/2001  Gelfand et al. ............. 435/194

FOREIGN PATENT DOCUMENTS

| EP | 0 892 058 A2 | 3/1998 | ............ C12N/15/54 |
| WO | PCT/US94/14065 | 12/1994 | ............ C12N/9/12 |
| WO | WO 95/16028 | * 6/1995 | |
| WO | PCT/US97/01656 | 2/1997 | ............ C12Q/1/68 |
| WO | PCT/EP97/01476 | 3/1997 | ............ C12N/15/54 |
| WO | PCT/EP99/01674 | 3/1999 | ............ C12N/9/00 |

OTHER PUBLICATIONS

Erlich et al. Recent Advances in the Polymerase Chain Reaction, Science, Jun. 1991, vol. 252, pp 1643–1652.*
Eur J Biochem. vol. 231 (1) 1995 Moussy G et al. "Interspecies DNA polymerase & chimeras are functional in Saccharomyces cerevisiae", pp. 45–49.

* cited by examiner

Primary Examiner—Richard Hutson
(74) Attorney, Agent, or Firm—Rick Martin; Patent Law Offices of Rick Martin, P.C.

(57) ABSTRACT

The present invention relates to an enzyme which has the properties of thermostability, DNA polymerase activity and proof-reading, said properties being derived from at least two different sources, wherein the properties are preferably in synergistic combination. Further, the invention relates to a thermostable DNA polymerase, wherein the enzyme contains a proof-reading function derived from an enzyme of one species and a polymerase function derived from an enzyme of a different species.

3 Claims, 5 Drawing Sheets

THERMOSTABLE DNA POLYMERASE

RELATED APPLICATIONS

This application claims priority under the Paris Convention from application serial number 9818432.8 which was filed in the United Kingdom on Aug. 24, 1998.

BACKGROUND OF THE INVENTION

The present invention relates to thermostable DNA polymerases, polynucleotide sequences encoding them, and methods for their manufacture.

DNA polymerases are well known, and are generally commercially available in purified form. These enzymes are useful in a wide range of laboratory processes, especially in molecular biology. Primer extension techniques, nucleic acid sequencing and the polymerase chain reaction (PCR) all employ such enzymes.

Thermostable DNA polymerases are particularly useful in a number of these techniques, as thermostable enzymes are able to be used at relatively high temperatures. This has benefits with respect to fidelity of primer binding, for example, owing to the high stringency of the conditions employed. Of known enzymes, the DNA polymerase isolated from *Thermus aquaticus* (Taq) is perhaps the best characterized. In addition, DNA polymerases have been isolated from other thermophilic bacteria, such as *Thermococcus litoralis, Thermus thermophilus* (T.th) and *Pyrococcus furiosus* (Pfu).

The available, purified enzymes have a defined range of different properties and limitations. Taq DNA polymerase, for example, has no proof-reading activity, which results in errors during DNA amplification. Native Pfu DNA polymerase has lower thermostability than Taq DNA polymerase, so that it loses activity faster than Taq DNA polymerase under similar conditions. In addition, Pfu DNA polymerase has a proofreading ability which reduces the rate of incorporation of the enzyme, which in turn reduces the processivity of the enzyme. The reduced thermostability in combination with the reduced processivity has the effect of reducing the length of the fragments that may be amplified by Pfu DNA polymerase, in comparison with Taq DNA polymerase. Therefore, neither Taq nor Pfu DNA polymerase have optimum properties for use in DNA amplification procedures.

Combinations of enzymes, such as mixtures of Taq DNA polymerase and Pfu DNA polymerase, have been used to try to obtain the combined benefits of both enzymes, but such mixtures are still subject to the limitations of each individual enzyme in the mixture. Moreover, commercial products using two enzymes are inevitably more expensive and there is a more stringent burden upon quality control to ensure that both enzymes have the necessary level of enzyme activity.

Thus, there is still a need for a single thermostable DNA polymerase with a combination of desirable properties that do not occur in nature.

SUMMARY OF THE INVENTION

We have now, surprisingly discovered that a functional, thermostable, chimaeric enzyme that overcomes the above problems may be obtained by combining functionalities of different enzymes.

Thus, in a first aspect, the present invention provides an enzyme which has the properties of thermostability, DNA polymerase activity and proof-reading, said properties being derived from at least two different sources, wherein the properties are preferably in synergistic combination.

In an alternative aspect, the present invention provides an enzyme which has the properties of thermostability, DNA polymerase activity and proof-reading, said properties being derived from at least two different polypeptides.

DETAILED DESCRIPTION OF THE INVENTION

The present invention will be illustrated with respect to the accompanying, non-limiting Figures, in which.

Figure 1:
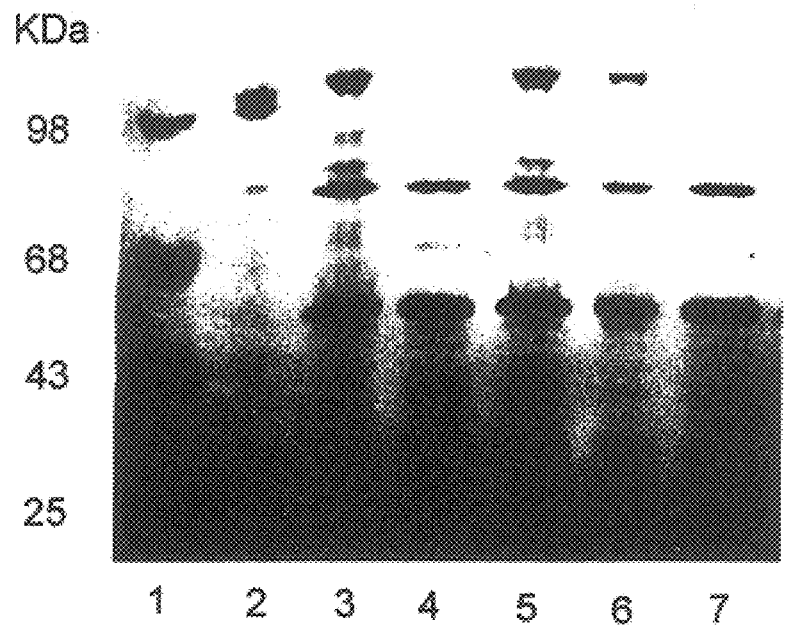
FIG. 1 is a photograph of a 10% SDS-polyacrylamide gel, to identify those samples that express a protein product of the chimaeric Pfu-Taq polymerase of the desired size.

The term 'thermostable', as used herein, refers to the ability of an enzyme to retain a level of its activity, at temperatures in excess of 37° C., for a significant length of time. The enzymes of the present invention are suitably selected for activity above 40° C., but more usefully are selected for activity at least above 70° C. or even 80° C., but enzymes retaining at least some activity above 90° C. are most preferred. A significant length of time is one that allows use of the activity of the enzyme in an appropriate technique, such as those described above, at the given temperature, before all activity is lost. In general, such activity will be measured by the amount of times a given step in a technique can be repeated. Preferred enzymes are able to be recycled in such techniques at least ten times prior to losing useful activity, more preferably at least 30 times.

In the case of thermostability, it will be appreciated that there is no guarantee that the ligation of protein fragments from different, thermostable enzymes will produce a daughter enzyme which is also thermostable. This is because the properties of an enzyme are related to the whole 3D structure of the enzyme. Merely taking two separate domains provides no guarantee of thermostability.

In the best case scenario, the thermostability of a chimaeric enzyme would be predicted to be that of the parent polypeptide having the lowest thermostability. For example, if one parent polypeptide were stable for long periods at 95° C. and the other parent polypeptide only stable for short periods at 90° C., then the resulting enzyme would be expected to be only stable for short periods at 90° C. Essentially, a chimaeric polypeptide would be expected to be only as thermostable as the least thermostable element or domain. This is especially true for chimaeric enzymes composed of a number of different domains taken from different parent polypeptides. Once the least thermostable domain has started to denature, all enzyme properties would be affected.

We prefer that the chimaeric enzyme is at least as thermostable as the parent polypeptide with the lowest thermostability. However, in the present invention, we have found that it is possible to maintain a level of thermostability near to that of the polypeptide having the greater thermostability, such as with the Taq (polymerase)/Pfu (proof-reading) chimaera and also the T.th (polymerase)/Pfu (proof-reading) chimaera. We particularly prefer that the chimaeric enzyme is more thermostable than at least one of the parental peptides or proteins.

It will be appreciated that the thermostability of the enzyme is a highly important factor for reactions that must be carried out at extreme temperatures. For example, some species of DNA, such as DNA with a high G+C base content, must be denatured at very high temperatures such as 98° C. An enzyme which denatures at such high temperatures will not be suitable for amplification reactions involving DNA of this nature.

It is known that mutation's of Pfu DNA polymerase can increase the thermostability of the enzyme. For example, the exo strain of Pfu DNA polymerase has a higher thermostability than native Pfu DNA polymerase, and can operate at 98° C. [Chong et al., American Journal of Medical Genetics, 51: 522–526, 1994]. The exonuclease portion of the enzyme thus contributes to lower the overall thermostability, as removal of this fragment increases thermostability. Surprisingly, in the present invention, the proofreading (exonuclease) portion of Pfu has been joined to a portion of Taq DNA polymerase or T.th DNA polymerase, while still maintaining the same thermostability as either of Taq and T.th DNA polymerase, with the same advantageous properties.

An enzyme having 'DNA polymerase activity' is one which is capable of catalyzing the synthesis of a chain of DNA from a single stranded DNA template, by nucleotide condensation. It will be appreciated that the enzymes of the present invention are necessarily DNA polymerases, and will generally be referred to as such, or even merely as polymerases, herein.

The term 'proof-reading' involves the exonuclease activity of the enzyme, and is used to indicate that the enzyme is capable of at least some error correction during transcription.

By 'synergistic combination' is meant that the combined properties of the enzyme are, in some way, enhanced over the expected sum of the individual parts. It will be appreciated that an enzyme can have a synergistic combination of properties, even where one property is not as great as the polypeptide from which it derives, if one or both of the other properties is sufficiently enhanced to compensate.

The other properties of polymerase activity and proof-reading may also be similarly enhanced, such as to obtain effectively error-free transcription, for example, or to allow transcription of even longer DNA fragments than the parent polymerase.

The properties of the enzymes of the present invention are derived from at least two different sources. Thus, it is possible that thermostability is derived from a first source, polymerase activity from a second, and proof-reading from a third. This does not preclude the possibility of further properties being derived from yet further sources, or of deriving one property from two different sources, or two properties from one source, provided that the third is obtained from a separate source. For example, where polymerase and proof-reading are derived from two thermostable sources, then, not only is it likely that the resulting enzyme is thermostable, but such thermostability will have been derived from two sources, and it is unlikely that it will be necessary to derive thermostability from a third source. Likewise, it is conceivable that more than one polymerase or proof-reading functionality may be present, although this is only likely to be useful in specialized circumstances, and is likely to increase the cost of the final product.

The sources from which the properties are derived are any that are capable of providing such properties. Such sources will generally be enzymes, at least in the case of the polymerase and proof-reading activities, but may also be carriers of enzyme domains, for example, which may not be active in their own right. Properties derived from different sources are properties derived from different peptides or polypeptides, such as enzymes, wherein the different peptides may be from the same or different species, but will generally be enzymes sharing a similar functionality, particularly polymerase activity, a suitable part or whole (or more) of a domain being selected from each.

More particularly, the properties will tend to be obtained by genetic engineering from such sources so that, while it is generally preferable that the polymerase and proof-reading activities of the enzyme essentially correspond directly to those of the source and/or which are found in nature, it will be appreciated that suitably modified functionalities may be employed. Suitable modifications are described below, but typically arise from the practicalities of genetic engineering, such as through the introduction of restriction sites and elimination and or changing of areas that might give rise to problems, for example.

We generally prefer that each derived activity comprises a structurally intact domain of a protein, but it will be appreciated that any length of a given domain sufficient to confer the desired activity on the enzyme of the invention may be used. For example, where activities from different sources are introduced into a host molecule, or where activities are directly ligated, it is entirely possible that an incomplete activity from one source may be completed by the sequence to which that activity is ligated. Similarly, an incomplete activity may be completed by genetic engineering, or an otherwise complete activity may be similarly supplemented.

It will be appreciated that the present invention also extends to mutants and variants of any such regions, including deletions, insertions, inversions and substitutions.

In a further aspect, the present invention provides a thermostable DNA polymerase, wherein the enzyme contains a proof-reading function derived from an enzyme of one species and a polymerase function derived from an enzyme of a different species.

We prefer that the enzyme is a chimaera containing Taq DNA polymerase activity and Pfu DNA polymerase proof-reading activity, wherein the proof-reading activity is derived from the Pfu DNA polymerase. In an alternative preferred embodiment the enzyme is a chimaera containing T.th DNA polymerase activity and Pfu DNA polymerase proof-reading activity. We particularly prefer that the enzyme of the invention essentially consists of Taq DNA polymerase/Pfu DNA polymerase chimaera or T.th DNA polymerase /Pfu DNA polymerase chimaera. Enzymes combining proof-reading activity from a different DNA polymerase gene into the Taq DNA polymerase gene, and enzymes combining polymerase activity from an enzyme other than Taq DNA polymerase or T.th DNA polymerase with the proof-reading portion of the Pfu DNA polymerase enzyme, are also preferred.

The preferred Pfu/Taq chimaeric enzyme has been found to be considerably more stable than Pfu DNA polymerase and about, or more, stable than Taq DNA polymerase. The enzyme is able to amplify fragments that are at least as long as those which may be amplified by Taq DNA polymerase. Further, the chimaeric enzyme has a higher fidelity than Taq DNA polymerase.

The preferred Pfu/T.th chimaeric enzyme has also been found to be considerably more stable than Pfu DNA polymerase and about, or more, stable than Taq DNA polymerase. Further, the chimaeric enzyme has a higher fidelity than Taq DNA polymerase, as measured by relative mutation rate.

We prefer that the chimaeric enzyme has a fidelity of DNA replication which is at least as good as the parent DNA polymerase with the lowest fidelity. In parallel with considerations of thermostability, it will be appreciated that there is no guarantee that the ligation of protein fragments from different polymerase enzymes will produce a daughter enzyme which a fidelity of replication which is comparable to that of any parent.

We also prefer that the enzyme is able to catalyze the production of 'long' DNA fragments, and is at least as good as Taq DNA polymerase. Taq DNA polymerase is able to catalyze the production of DNA fragments of up to approximately 10 kb, using lambda DNA as a template. Under similar conditions, native Pfu DNA polymerase can catalyze the production of approximately 2 kb. We particularly prefer that the chimaeric enzyme of the present invention can catalyze the production of DNA of more then 10 kb, preferably more than 15 kb and most preferably more than 20 kb.

In a preferred embodiment, the chimaeric enzyme comprises amino acids 4–376 of *P. furiosus* DNA polymerase I, and amino acids 238–832 from *T. aquaticus* DNA polymerase I. These lengths have been established empirically, and it will be appreciated that longer and/or shorter lengths are likely to provide equivalent activity, the length of each sequence being readily determined by those skilled in the art.

In the preferred embodiment, the enzyme contains a Ser-Gly-Asp-Leu linker between the Pfu and Taq domains. However, other linkers will be apparent to those skilled in the art. The resulting enzyme has 3'–5' exonuclease (proofreading) activity, which increases the fidelity of the enzyme with respect to Taq DNA polymerase. The DNA produced by the chimaeric enzyme has a five-fold reduction in error rate when compared with Taq DNA polymerase. Further, the chimaeric enzyme is at least as thermostable as Taq DNA polymerase, and more thermostable than Pfu DNA polymerase.

In a further preferred embodiment, the enzyme comprises amino acids 4–376 of *P. furiosus* DNA polymerase I, and amino acids 240'834 from *Thermus thermophilus* DNA polymerase I. Similar considerations as with the previous preferred embodiment apply, *mutatis mutandis*. This enzyme contains a Ser-Gly-Asp-Leu linker between the Pfu and T.th domains, although it will be appreciated that other linkers will be apparent to those skilled in the art. The resulting enzyme has 3'–5' exonuclease (proof-reading) activity, which increases the fidelity of the enzyme with respect to Taq DNA polymerase. The DNA produced by this chimaeric enzyme has a reduction in error rate (approximately 2 fold) when compared with Taq DNA polymerase. The chimaeric enzyme is, additionally, at least as thermostable as Taq DNA polymerase, and more thermostable than Pfu DNA polymerase.

It will be appreciated that a chimaeric protein may be constructed in a number of ways, most easily via the construction of a recombinant DNA molecule, followed by expression of the protein product. Manipulation at the DNA level allows DNA fragments from different genes to be joined together by ligation, to form DNA encoding a chimaeric polymerase. DNA fragments from different DNA polymerase genes may be obtained by DNA purification, followed by restriction enzyme digestion, PCR, or even direct DNA synthesis, for example. The protein may then be. expressed from the DNA, using expression vectors maintained within host cells. DNA cloning, manipulation and protein expression are all standard techniques in the art, and details of suitable techniques may be found in Sambrook et al, 'Molecular cloning—A Laboratory Handbook', 1989.

The present invention, therefore, also provides DNA and RNA encoding the thermostable DNA polymerase, along with vectors containing the DNA, host cells containing these vectors, and cultures of such cells, as well as methods for making the enzyme. The invention also includes nucleic acid species which hybridize to DNA encoding the protein of the invention, hybridization being carried out under standard conditions, preferably 60° C. and 6×SSC. Additionally, the present invention includes kits containing the enzyme of the invention in combination with other reagents, suitable for use in laboratory experiments.

DNA and vectors encoding all or part of an enzyme of the invention may suitably incorporate such control elements, such as start/stop codons, promoters etc. as are deemed necessary or useful, as the skilled person desires. Suitable constructs are illustrated in the accompanying Examples.

The Examples are illustrative of, but not binding on, the present invention. Any methods, preparations, solutions and such like which are not specifically defined may be found in Sambrook et al., (supra). All solutions are aqueous and made up in sterile, deionized water, unless otherwise specified. All enzymes were obtained from the Laboratory of Biotechnology (Institute of Bioorganic Chemistry, RAS), with the exception of Sequenase, which was obtained from Amersham and *Pyrococcus furiosus* strain Vc1 which was obtained from the Deutsche Sammlung von Mikroorganismen [Fiala, G. and Stetter, K. O. (1986) Arch. Microbiol., 145, 56–61].

Examples 1–6 relate to the production and testing of a Pfu-Taq chimaeric polymerase. Examples 7–11 relate to similar production and testing of a Pfu-T.th chimaeric polymerase.

EXAMPLE 1

Cloning of the Pfu DNA Fragment

A chimaeric enzyme was constructed, comprising a portion of the Pfu DNA polymerase gene and a portion of the Taq gene. In more detail, the procedure was as follows, in this and the following Examples.

A fragment of *Pyrococcus furiosus* DNA polymerase [Uemori, T. et al., (1993), N. A. R., 21, 2, 259–265], representing amino acids 4 to 376, was obtained by PCR amplification of total Pyrococcusfuriosus DNA, primed by the two synthetic DNA primers PrPFUN and PrPFUC (below). Total DNA from *Pyrococcus furiosus* was isolated by the phenol deproteinization method. The primers used were:

PrPFUN
5'-AAACCCGGGATGTGGATTACATAACTGAA GAA-3'[SEQ ID NO 5]

PrPFUC 5'-AAAAAGTACTCCTCTTCACTTG-3'[SEQ ID NO 6]

Primer PrPFUN is homologous to wild type DNA starting at codon 4; this primer is designed to incorporate a Sma I site into the amplified DNA product. Primer PrPFUC is homologous to codons 372–376 on the non-coding strand of the wild-type gene encoding *Pyrococcus furiosus* DNA polymerase [Uemori, T., et al., supra] and is designed to incorporate a Sca I site into amplified fragment.

PCR was performed using a DNA Thermal Cycler 480 (Perkin-Elmer-Cetus). The reaction mixture (50 µl) contained 67 mM Tris-HCl (pH 8.8), 16.6 mM $(NH_4)_2SO_4$, 0.01% Tween-20, 0.2 mM of each dNTP's, 3.5 mM $MgCl_2$, 10 pmol of each primer, 10 ng of DNA as a template, and 5 U of Taq DNA polymerase. The reaction included 25 cycles: 94° C.—30 s; 58° C.—30 s; 72° C.—100 s.

The amplified fragment was purified by 2% w/v agarose-gel electrophoresis, phenol extraction and was precipitated by ethanol. It was then digested with restriction endonucleases Sma I and Sca I.

EXAMPLE 2

Cloning of the Tag DNA Fragment (Plasmid pKTAQ4)

A fragment of *Thermus aquaticus* YT1 DNA polymerase [Lawyer, F. C. et al., J. Biol. Chem., 261, 11, 6427–6437] comprising amino acids 238 to 852 was obtained by PCR amplification of total *Thermus aquaticus* YT1 DNA, primed by the two synthetic DNA primers PrKTAN and PrKTAC. Total DNA from *Thermus aquaticus* YT1 was isolated by the phenol deproteinization method [Sambrook et al., supra].

Primer PrKTAN 5'AGATCTGGACGATCT-GAAGCTCTCCTGGGAC [SEQ ID NO 7] is homologous to wild type *Thermus aquaticus* YT1 DNA [Lawyer et al., supra] starting at codon 238 of the DNA polymerase gene, this primer is designed to incorporate a Bgl II site into the amplified DNA product. Primer PrKTAC 5'-GTCGACTATCACTCCTTGGCCGGAGAGCCA [SEQ ID NO 8] is homologous to codons 848–852 on the other strand of the wild-type gene encoding *Thermus aquaticus* YT1 DNA polymerase and is designed to incorporated a SalG I site and a stop codon into the amplified fragment.

PCR was performed using a DNA Thermal Cycler 480 (Perkin-Elmer-Cetus). The reaction mixture (50 µl) contained 67 mM Tris-HCl (pH 8.8), 16.6 mM $(NH_4)_2SO_4$, 0.01% v/v Tween-20, 0.2 mM of each dNTP's, 3.5 mM $MgCl_2$, 10 pmol of each primer, 10 ng of DNA as a template, and 5 U of Taq DNA polymerase. The reaction included 25 cycles: 94° C.—30 s; 58° C.—30 s; 72° C.—150 s.

The amplified fragment was purified by 1.5% w/v agarose-gel electrophoresis and phenol extraction, and was then precipitated by ethanol. The fragments were digested with restriction endonucleases Bgl II and SalG I and ligated into plasmid pUC18 [Yanish-Perron et al., (1985), Gene, 33, 103–119] which had been digested with the BamH I and salG I restriction enzymes and previously treated with calf intestinal alkaline phosphatase [Sambrook et al., supra].

Ligation was conducted with T4 DNA ligase [Moore S. K., and James, E., (1976), Anal. Biochem., 75, 545–554] in a 50 µl volume containing 200 ng vector (plasmid pUC 18) and 200 ng of the insert. *E. coli* JM 109 cells were transformed with the ligation mixture according to the method of Dower et al. [1988, Nucl. Acid. Res., 16, 1127]. Transformed cells were grown on LB medium, and expression of the cloned gene was induced by 0.125 mM IPTG. Clones were selected from ampicillin resistant colonies and checked to determine which ones contained the Taq DNA polymerase gene insert. Positives were assayed for production of protein of the corresponding MW by 12% SDS-polyacrylamide gel electrophoreses [Laemmli U., (1970), Nature 227, 680–685]. Five positives were grown to an optical density of $A_{600}$ 0.4 in 500 ml of LB medium containing ampicillin (75 µg/ml) at 37° C. Protein synthesis was induced by 0.125 mM IPTG. The cells were further incubated for 4 h at 37° C. Cells were harvested by centrifugation and the enzyme was partially purified as follows.

All samples were isolated at 4° C. Cells (0.5 g) were suspended in 2 ml of buffer A (20 mM K-phosphate pH 7.0, 2 mM DTT, 0.5 mM EDTA) containing 0.2M NaCl and 0.1 mM phenylmethylsulphonyl.fluoride (PMSF). The cells were disrupted by ultrasonic disintegration (MSE, 150 wt) at maximum amplitude for 15 sec (3 impulses, each for 5 sec) with cooling on ice. The suspension was centrifuged at 20,000 g, the supernatant collected, and 5% v/v polyethylenimine was added to a final concentration of 0.1% v/v. The resulting precipitate was separated by centrifugation, and the supernatant removed. The supernatant proteins were then precipitated by solid ammonium sulfate at 75% saturation. The polymerase-containing precipitate was collected by centrifugation at 20,000 g, dissolved in 3 ml of buffer A, containing 0.1 M NaCl and 0.2% Tween-20, then heated for 5 minutes at 75° C. and centrifuged (10 min, 20,000 g). Denatured proteins were discarded and supernatant was assayed by its ability to perform PCR. A plasmid was isolated and purified from cells in which truncated Taq polymerase was active in PCR. PCR assays were conducted using a DNA thermal cycler 480 (Perkin Elmer-Cetus).

The reaction mixture (50 g) contained 67 mM Tris-HCl (pH 8.8 at 25° C.), 16.6 mM $(NH_4)_2SO_4$, 0.01% Tween-20, 0.2 mM each DNTP, 4 mM $MgCl_2$, 10 pmol each primer (Prλ1: 5'-GATGAGTTCGTGTCCGTACAACTGG-3'[SEQ ID NO 9] and Prλ6: 5'-GGTTATCGAAATCAGCCACAGCGCC-3'[SEQ ID NO 10]), 50 ng template lambda DNA and 2 µl of the above supernatant containing the enzyme. 30 cycles of the following cycle was carried out; 93° C. for 30 seconds, 57° C. for 40 seconds and 72 ° C. for 30 seconds. The plasmid was designated pKTAQ4.

EXAMPLE 3

Preparation of an Expression Vector (plasmid pCHIE1)

The Sma I/ScaI fragment (see Example 1) was cloned into plasmid pKTAQ4, as follows.

Before ligation, plasmid pKTAQ4 was cut with restriction endonuclease Kpn I and the 3'-overhang was filled in with the Klenow fragment [Klenow, H., and Henningsen, I., (1970), Proc. Natl. Acad. Sci., USA, 65, 168–175]. Ligation was carried out using T4 DNA ligase in a 50 µl volume containing 200 ng vector (plasmid pKTAQ4) and 200 ng SmaI/ScaI fragment of the Pfu DNA polymerase gene obtained in Example 1. *E. coli* cells JM 109 were transformed with the ligase mixture according to the method of Dower et al., (supra). Transformed cells were grown on LB medium. Expression of the cloned gene was induced by 0.125 mM IPTG. Ampicillin resistant colonies arising from the transformation were selected. The clones which contained the Pfu DNA polymerase gene insert were selected by PCR using DNA from assayed cells and primers PrPFUN and PrPFUC (see Example 1).

Plasmids containing the Pfu insert were assayed for production of protein of the predicted MW by SDS-acrylamide gel electrophoresis (FIG. 1). In three positives, the induced proteins were of the expected size (110–120 kDa) and these were grown in 1 liter of LB medium containing ampicillin (75 $\mu$l/ml) at 37° C. to an optical density of $A_{600}$ 0.4. Protein synthesis was then induced by 0.125 mM IPTG. The cells were kept for 4 h at 37° C., then the cells were harvested by centrifugation. The enzyme was then partly purified by following procedure.

All samples were isolated at 4° C. Cells (1 g) were suspended in 3 ml of buffer A (supra) containing 0.2M NaCl and 0.1 mM PMSF. The cells were disrupted using ultrasonic disintegrator (MSE, 150 wt) at maximum amplitude for 15 sec (3 impulses, each for 5 sec) and with cooling on ice. The suspension was centrifuged at 20,000 g, after which 5% polyethylenimine was added to the supernatant to a final concentration of 0.1%. The resulting precipitate was separated by centrifugation and the remaining supernatant removed. Proteins were then precipitated by ammonium sulfate at 50% saturation. The polymerase-containing precipitate was collected by centrifugation at 20,000 g, dissolved in buffer A (3 ml) containing 0.1 M NaCl and 0.2% Tween-20, then heated for 5 minutes at 75° C. and centrifuged (10 min, 20,000 g). Denatured proteins were discarded and the supernatant was assayed for its ability to perform PCR.

Figure 2:
FIG. 2 is a photograph of an agarose gel, which compares the PCR amplification obtainable by Taq DNA polymerase, Pfti DNA polymerase and a preferred embodiment of the DNA polymerase (Pfu/Taq chimaeric enzyme) of this invention, under different conditions.
Figure 3:
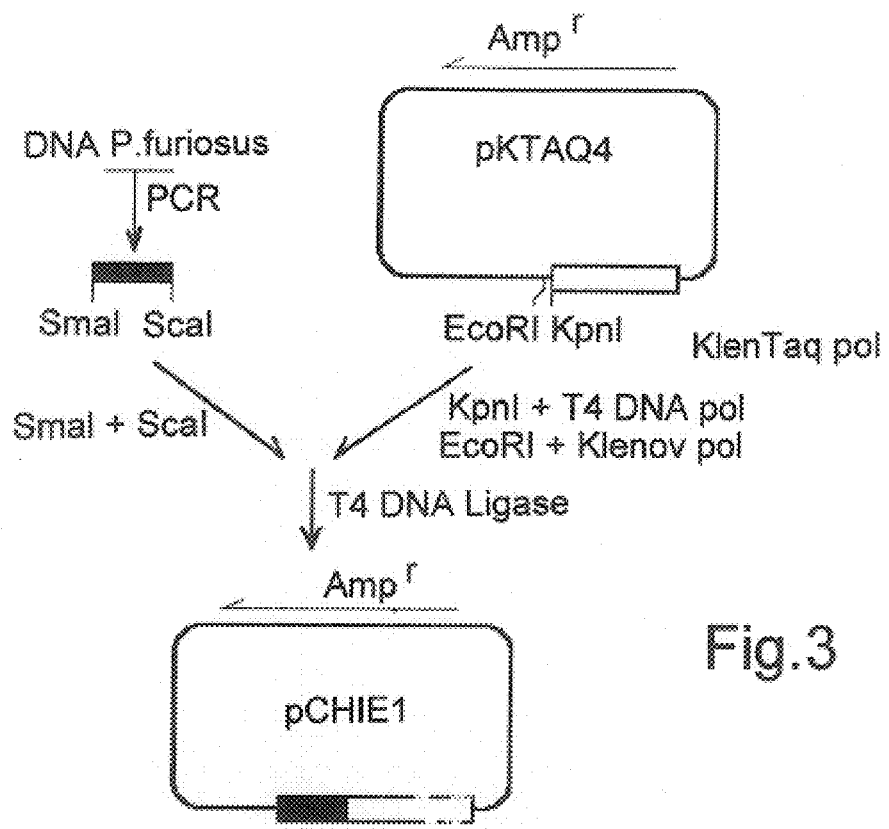
FIG. 3 is a scheme illustrating steps in construction of plasmid pCHIE1, and its physical map.

PCR amplification [Saiki, R. K., et al., (1985), Science, 230, 1350–1354] was performed using a DNA Thermal Cycler 480 (Perkin-Elmer Cetus). The reaction mixture (50 $\mu$l) contained 67 mM Tris-HCl (pH 8.8 at 25° C.), 16.6 mM $(NH_4)_2SO_4$, 0.01% Tween-20, 0.2 mM of each dNTP, 3.5 mM $MgCl_2$, 10 pmol of primers Pr$\lambda$1 and Pr$\lambda$6, as in Example 6, 10 ng of lambda DNA as a template, and 5 U of chimaeric DNA polymerase. The reaction included 25 cycles of: 94° C.—30 s; 58° C.—30 s; 72° C.—100 s. Plasmid DNA was isolated from cells which produced a chimaeric enzyme that was active in PCR (FIG. 2). The plasmid was ftrrther purified, and designated pCHIE1. The construction of pCHIE1 is shown in FIG. 3.

The data in FIG. 2 indicate that the chimaeric enzyme of the invention is more thermostable than the Pfu DNA polymerase. In lane 2, the PCR reaction was carried out with Pfu DNA polymerase preheated to 95° C. No product was observed. In contrast, in lane 5, preheating of the chimaeric enzyme had no effect on the ability of the enzyme to function in the PCR reaction. This indicates that the chimaeric enzyme of the invention is more thermostable than Pfu DNA polymerase.

EXAMPLE 4

Preparation of Chimaeric Pfu/Taq Enzyme Using an Expression Vector (Plasmid pCHIE1)

Plasmid pCHIE1 contains the following regions: the lac promoter; an ATG start codon; the *E. coli* LacZ' sequence for codons Thr Met Ile Asn; an inserted tryptophan codon; codons 4–376 of Pfu DNA polymerase; a Ser-Gly-Asp-Leu linker; codons 238–832 of *Thermus aquaticus* YT1 DNA polymerase; followed by the stop codon TGA. This pUC18 based vector also encodes ampicillin resistance (FIG. 3).

Cells (35g) containing the plasmid were suspended in 70 ml of buffer A (20 mM K-phosphate pH 7.0, 2 mM DTT, 0.5 mM EDTA) containing 0.2M NaCl and 0.1 mM PMSF. The cellular walls were disrupted with an ultrasonic disintegrator (MSE, 150 wt) at maximum amplitude for 15 minutes (30 impulses, each for 30 sec) and with cooling on ice. The suspension was then centrifuged at 40,000 g, the pellet discarded, and 5% polyethylenimine was added to the supernatant to a final concentration of 0.1%. The precipitate was separated by centrifugation, and the remaining proteins precipitated with ammonium sulfate at 45% saturation. The resulting polymerase-containing precipitate was collected by centrifugation at 20,000g and dissolved in buffer A (30 ml) containing 0.1 M NaCl and 0.2% Tween-20, heated for 15 minutes at 75° C. in the presence of 10 mM $MgCl_2$, and centrifuged for 10 minutes at 40,000 g.

The supernatant was loaded on to a (2.5×20 cm) phosphocellulose P-11 column (Whatman) equilibrated in buffer A containing 0.1 M NaCl, and washed out with the same buffer. The proteins were eluted with a linear gradient of NaCl concentrations ranging from 100 to 500 mM in buffer A. The gradient volume was 800 ml, and the flow rate was 60 ml/h. Polymerase was eluted at NaCl concentrations ranging from 280 to 330 mM.

The fractions were tested for Polymerase activity, assayed via inclusion of the radioactive-labeled nucleotide $^{32}P$ (DATP) into the acid-insoluble pellet [Myers T. W., Gelfand D. H., (1991) Biochemistry, v30, N31, p7661–7666].

Specifically, the amount of the enzyme that incorporated 10 nmol of deoxynucleotide triphosphates into the acid-insoluble fraction within 30 minutes under conditions described below was taken as one unit of activity. The reaction mixture (50 $\mu$l) contained 25 mM N-Tris [Hydroxymethyl] methyl-3-aminopropanesulphonic acid (TAPS), pH 9.3, 50 nM KCl, 3.5 mM $MgCl_2$; 1 mM P-mercaptoethanol; 0.2 mM of each dNTP's, 1 $\mu$Ci $^{32}P$ (dATP), and 12.5 $\mu$g of activated salmon sperm DNA. Salmon sperm DNA (12.5 mg/ml) was activated in 10 mM Tris-HCl (pH 7.2) containing 5 mM $MgCl_2$ with pancreatic DNase I (0.03 U/ml) at 4° C. for 1 h and then heated at 95° C. for 5 minutes The polymer so activity was determined at 73° C.

Fractions containing the polymerase were combined, dialyzed against buffer A containing 50 mM NaCl and loaded on to a column (0.6×6 cm) of DEAE-cellulose (Whatman) equilibrated with same buffer. The proteins were eluted with a linear gradient of NaCl concentrations ranging from 50 to 250 mM in buffer A. The gradient volume was 150 ml, and the flow rate was 15 ml/h. The polymerase was eluted at 150–200 mM NaCl.

The purified enzymes were stored at −20° C. in the following buffer: 100 mM NaCl; 10 mM Tris HCl pH 7.5; ImM DTT; 0.2% Tween 20 and 50% (v/v) glycerol.

Figure 4:
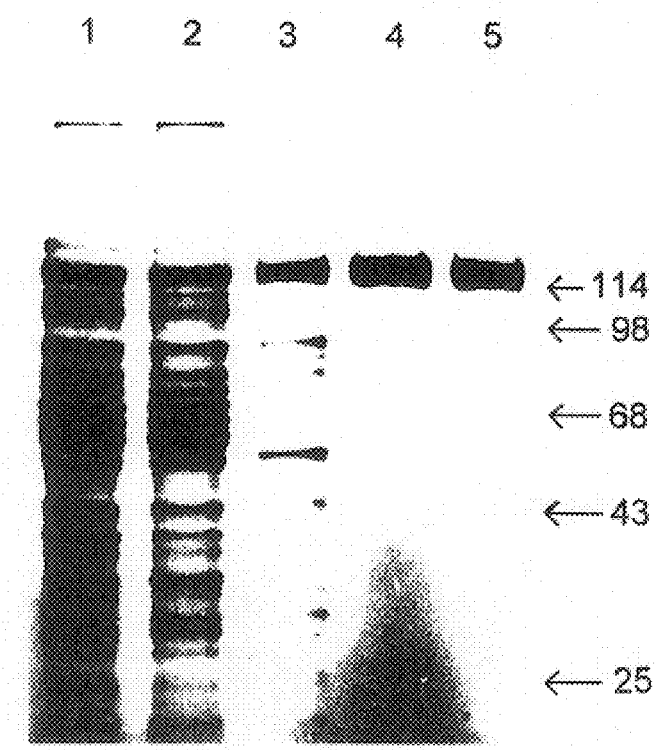
FIG. 4 is a photograph of a 10% SDS-polyacrylamide gel, showing the purification of the Pfu/Taq chimaeric polymerase samples.

Homogeneity of the polymerase preparations was not less than 95% according to SDS electrophoresis data on a 10% polyacrylamide gel (FIG. 4).

EXAMPLE 5

Polymerase Fidelity

Figure 6:
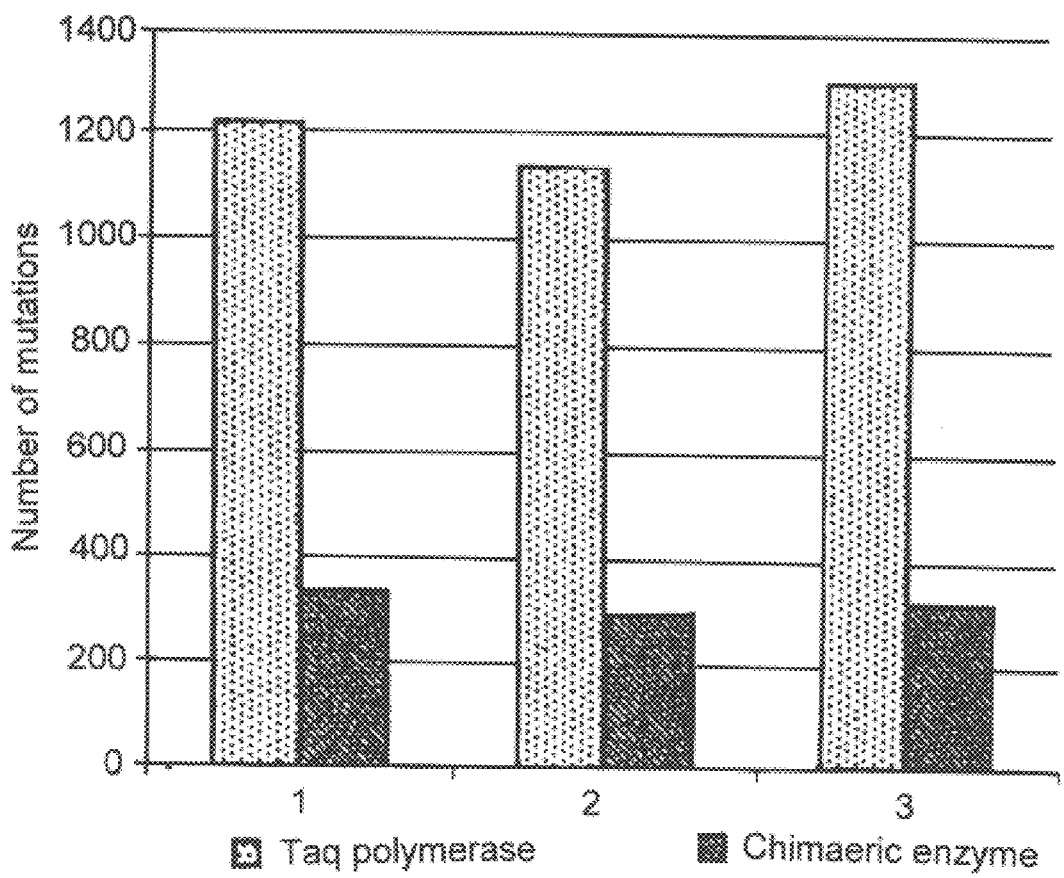
FIG. 6 shows the relative fidelity of the Pfu/Taq chimaeric enzyme in comparison to Taq DNA polymerase.

The fidelity of the chimaeric polymerase as produced in Example 4 was compared with that of Taq DNA polymerase. The fidelity was assessed using pUR222 using the method of Barnes, W. M. [(1992) Gene, 112, 29–35]. Results are shown in FIG. 6. The chimaeric enzyme had a five fold lower relative mutation rate, when compared to full length Taq DNA polymerase.

EXAMPLE 6

DNA Amplification

λ phage DNA was amplified using the primer pairs Prλ1 with Prλ6, or primer pairs Prλ1 with Prλ8. The primer sequences were as follows:

Prλ1: 5"-GATGAGTTCGTGTCCGTACAACTGG-3' [SEQ ID NO 9]

Prλ6: 5'-GGTTATCGAAATCAGCCACAGCGCC-3' [SEQ ID NO 10]

Prλ8 5'-TCGATCACACTCAGCAACTGCGTGG-3' [SEQ ID NO 11]

The Prλ1 and Prλ6 primers were predicted to produce a product of 500 base pairs. The Prλ1 and Prλ8 primers were predicted to produce a product of 8400 base pairs.

Each of Taq DNA polymerase, Pfu DNA polymerase and the chimaeric enzyme were used in a PCR reaction, with λ with DNA as a template. Each enzyme was used with both sets of primer pairs. The conditions used were as follows: PCR assays were conducted using a DNA thermal cycler 480 (Perkin Elmer-Cetus). The reaction mixture for Taq (50 µl) contained 67 mM Tris-HCl (pH 8.8 at 25° C.), 16.6 mM $(H_4)_2SO_4$, 0.01% Tween-20, 1.5 mM $MgCl_2$, 10% trehalose, 0.2 mM each DNTP, 10 pmol each primer, 100 ng template lambda DNA and 5U of Taq DNA polymerase. The reaction mix for Pfu DNA polymerase and the chimaeric enzyme (50 µl) contained 10 mM KCl, 10 mM $(NH_4)_2SO_4$, 20 mM Tris-HCl (pH 8.8 at 25° C.), 0.1% Triton X-100, 10% trehalose, either 2 mM (Pfu) or 4 mM (chimaeric) MgCl2, and 5U each DNA polymerase. 30 cycles of the following cycle was carried out; 92° C. for 30 seconds, 58° C. for 45 seconds and 72° C. for 4 minutes. After 30 cycles, aliquots from each reaction were loaded onto a 1% w/v agarose gel, stained by ethidium bromide and photographed under UV light.

The lanes were as follows:

Primers used: Lane 1, 3, and 5: Primers Prλ1 and Prλ6 Lane 2, 4 and 6: Primers Prλ1 and Prλ8

Figure 5:
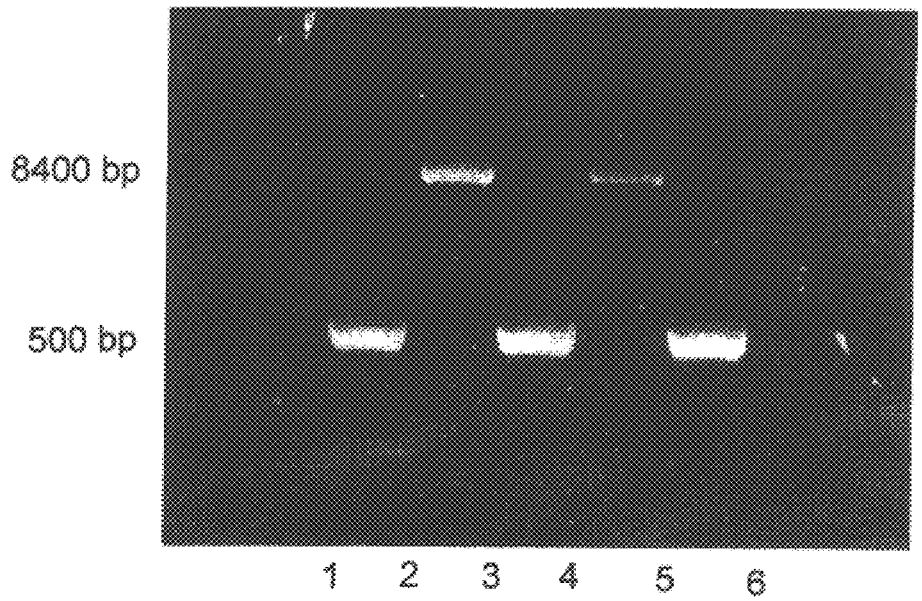
FIG. 5 shows the length of PCR products obtainable by Taq DNA polymerase, Pfu DNA polymerase and the chimaeric DNA polymerase.

Enzyme used: Lanes 1 and 2: chimaeric enzyme Lanes 3 and 4: Taq DNA polymerase Lanes 5 and 6: Pfu DNA polymerase The results are shown in FIG. 5, and indicate that the chimaeric enzyme of the invention is able to amplify DNA fragments of at least 8.4 kb. The chimaeric enzyme is, thus, able to amplify DNA fragments at least as large as those amplified by Taq DNA polymerase.

EXAMPLE 7

A chimaeric enzyme was constructed, comprising a portion of the Pfu DNA polymerase gene and a portion of the T.th DNA polymerase gene. In more detail, the procedure was as follows, in this and the following Examples.

Cloning of the T.th DNA Fragment (Plasmid pKTTH)

A fragment of *Thermus thermophilus* HB8 DNA [US-A-5789224, "Recombinant expression vectors and purification methods for *Thermus thermophilus* DNA polymerase", incorporated herein by reference] comprising amino acids 240 to 834 was obtained by PCR amplification of total *Thermus thermophilus* HB8 DNA, primed by the two synthetic DNA primers PrKTTN and PrKTATC. Total DNA from *Thermus thermophilus* HB8 was isolated by the phenol deproteinization method [Sambrook et al., supra].

Primer PrKTTN 5'-AGATCGGACGACCTCAGGCTCTCCTTGGAG-3' [SEQ ID NO 12] is homologous to wild type *Thermus thermophilus* HB8 DNA (U.S. Pat. No. 5789224) starting at codon 240 of the DNA polymerase gene. This primer is designed to incorporate a Bgl II site into the amplified DNA product. Primer PrKTATC 5'-GTCGACCTAACCCTTGGCGGAAAGCCA-3'[SEQ ID NO 13] is homologous to codons 818–834 on the other strand of the wild-type gene encoding *Thermus thermophilus* HB8 DNA polymerase and is designed to incorporated a SalG I site and a stop codon into the amplified fragment.

PCR was performed using a DNA Thermal Cycler 480 (Perkin-Elmer-Cetus). The reaction mixture (50 µl) contained 67 mM Tris-HCl (pH 8.8), 16.6 mM $(NH_4)_2SO_4$, 0.01% v/v Tween-20, 0.2 mM of each dNTP's, 3.5 mM $MgCl_2$, 10 pmol of each primer, 10 ng of DNA as a template, and 5 U of Taq DNA polymerase. The reaction included 25 cycles: 94° C.—30 s; 58° C.—30 s; 72° C.—150 s.

The amplified fragment was purified by 1.5% w/v agarose-gel electrophoresis and phenol extraction, and was then precipitated by ethanol. The fragments were digested with restriction endonucleases Bgl II and SalG I and ligated into plasmid pUC18 which had been digested with the BamH I and SalG I restriction enzymes and previously treated with calf intestinal alkaline.phosphatase [Sambrook et al., supra].

Ligation was conducted with T4 DNA ligase [Moore S. K., and James, E., (1976), Anal. Biochem., 75, 545–554] in a 50 µl volume containing 200 ng vector (plasmid pUC18) and 200 ng of the insert. *E. coli* JM 109 cells were transformed with the ligation mixture according to the method of Dower et al. (1988, Nucl. Acid. Res., 16, 1127). Transformed cells were grown on LB medium at 37° C., and expression of the cloned gene was induced by 0.125 mM IPTG. Clones were selected from ampicillin resistant colonies and checked to determine which ones contained the T.th DNA polymerase gene insert. Positives were grown to an optical density of $A_{600}$ 0.4 in 500 ml of LB medium containing ampicillin (75 µg/ml) at 37° C. Protein synthesis was induced by 0.125 mM IPTG. The cells were further incubated for 4 h at 37° C. Cells were harvested by centrifugation and the enzyme was partially purified as follows.

All samples were isolated at 4° C. Cells (0.5 g) were suspended in 2 ml of buffer A (20 mM K-phosphate pH 7.0, 2mM DTT, 0.5 mM EDTA) containing 0.2M NaCl and 0.1 mM phenylmethylsulphonylfluoride .(PMSF). The cells were disrupted by ultrasonic disintegration (MSE, 150 wt) at maximum amplitude for 15 sec (3 impulses, each for 5 sec) with cooling on ice. The suspension was centrifuged at 20,000g, the supernatant collected, and 5% v/v polyethylenimine was added to a final concentration of 0.1% v/v. The resulting precipitate was separated by centrifugation, and the supernatant removed. The supernatant proteins were then precipitated by solid ammonium sulfate at 75% saturation. The polymerase-containing precipitate was collected by centrifugation at 20,000 g, dissolved in 3 ml of buffer A, containing 0.1 M NaCl and 0.2% Tween-20, then heated for 5 minutes at 75° C and centrifuged (10 min, 20,000 g). Denatured proteins were discarded and supernatant was assayed by its ability to perform PCR.

PCR assays were conducted using a DNA thermal cycler 480 (Perkin Elmer-Cetus). The reaction mixture (30 µl)

contained 67 mM Tris-HCl (pH 8.8 at 25° C.), 16.6 mM $(NH_4)_2SO_4$, 0.01% Tween-20, 0.2 mM each dNTP, 4.5 mM $MgCl_2$, 10 pmol each primer (Prλ1 and Prλ6, as in Example 6), 20 ng template lambda DNA and 1 µl of the above supernatant containing the enzyme. 30 cycles of the following cycle was carried out; 93° for 30 seconds, 57° C. for 40 seconds and 72° C. for 30 seconds.

The plasmid was designated pKTTH.

EXAMPLE 8

Preparation of an Expression Vector (Plasmid pCHIE2)

The Sma I/ScaI fragment from Pfu (see Example 1) was cloned into plasmid pKTTH, as follows.

Before ligation, plasmid pKTTH was cut with restriction endonuclease Kpn I and the 3'-overhang was removed by T4 DNA polymerase [Challberg, M. D. and Englund, P. T. (1980) Methods in Enzymology 65, Ed. L. Grossman, K. Moldave, Acad. Press, N-Y, p.1, 39–43]. The plasmid was then digested with EcoRI and the 5' end was filled in by use of the Klenow fragment [Klenow, H. and Henningsen, I. (1970), P.N.A. S.65, 168–175]

Ligation was carried out using T4 DNA ligase in a 50 µl volume containing 200 ng vector (plasmid pKTTH) and 200 ng SmaI/ScaI fragment of the Pfu DNA polymerase gene obtained in Example 1. *E. coli* cells JM1 09 were transformed with the ligase mixture according to the method of Dower et al., (supra). Transformed cells were grown on LB medium. Expression of the cloned gene was induced by 0.125 mM IPTG. Ampicillin resistant colonies arising from the transformation were selected. The clones which contained the Pfu DNA polymerase gene insert were selected by PCR using DNA from assayed cells and primers PrPFUN and PrPFUC.

Figure 7:
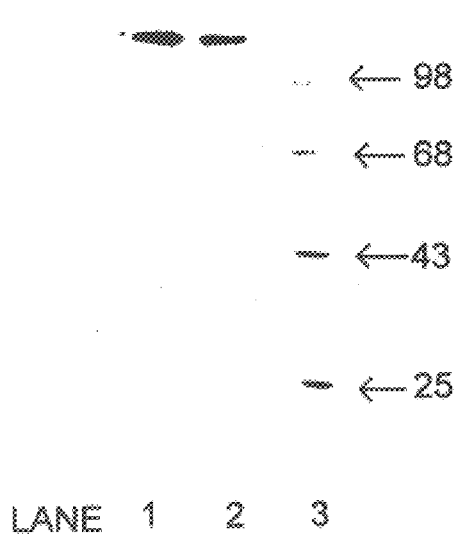
FIG. 7 is a photograph of a 10% SDS-polyacrylamide gel, to identify those samples that express a protein product of chimaeric Pfu-T.th polymerase the desired size.

Plasmids containing the Pfu insert were assayed for production of protein of the predicted MW by SDS-acrylamide gel electrophoresis (FIG. 7). In clones positive for both the presence of the gene and production of protein, the induced proteins were of the expected size (110–120 kDa) and these clones were grown in 1 liter of LB medium containing ampicillin (75 µl/ml) at 37° C. to an optical density of $A_{600}$ 0.4. Protein synthesis was then induced by 0.125 mM IPTG. The cells were kept for 4 h at 37° C., then the cells were harvested by centrifugation. The enzyme was then partly purified by following procedure.

All samples were isolated at 4° C. Cells (1 g) were suspended in 3 ml of buffer A (supra) containing 0.2M NaCl and 0.1 mM PMSF. The cells were disrupted using ultrasonic disintegrator (MSE, 150 wt) at maximum amplitude for 15 sec (3 impulses, each for 5 sec) and with cooling on ice. The suspension was centrifuged at 20,000 g, after which 5% polyethylenimine was added to the supernatant to a final concentration of 0.1%. The resulting precipitate was separated by centrifugation and the remaining supernatant removed. Proteins were then precipitated by ammonium sulfate at 50% saturation. The polymerase-containing precipitate was collected by centrifugation at 20,000 g, dissolved in buffer A (3 ml) containing 0.1 M NaCl and 0.2% Tween-20, then heated for 5 minutes at 75° C. and centrifuged (10 min, 20,000 g). Denatured proteins were discarded, and the supernatant was assayed for its ability to perform PCR. PCR amplification was performed using a DNA Thermal Cycler 480 (Perkin-Elmer Cetus). The reaction mixture (50 µl) contained 67 mM Tris-HCl (pH 8.8 at 25° C.), 16.6 mM $(NH_4)_2SO_4$, 0.01% Tween-20, 0.2 mM of each dNTP, 3.5 mM MgCl2, 10 pmol each of primers Prλ1 and Prλ6, 30ng of lambda DNA as a template. 25 cycles of the following cycle were then carried out: 94° C.—30 s; 58° C.—30 s; 72° C.—30 s.

Figure 8:
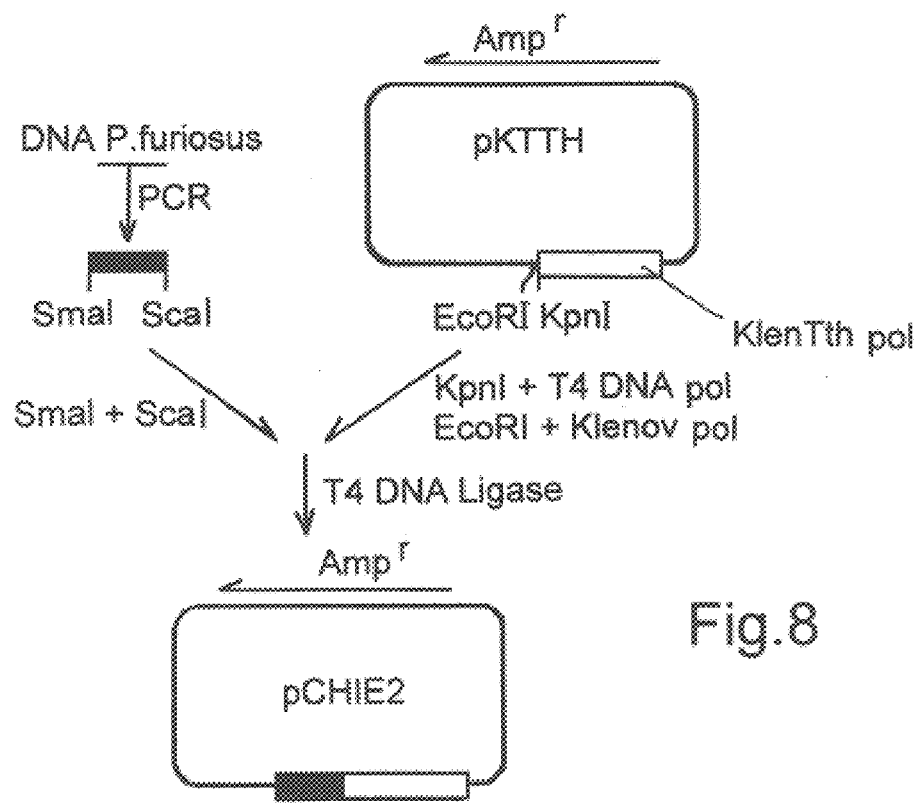
FIG. 8 is a scheme illustrating steps in construction of plasmid pCHIE2, and its physical map.

The plasmid was further purified, and designated pCHIE2. The construction of pCHIE2 is shown in FIG. 8.

EXAMPLE 9

Preparation of Chimaeric Pfu/T.th Enzyme Using an Expression Vector (Plasmid pCHIE2)

Plasmid pCHIE2 contains the following regions: the lac promoter; an ATG start codon; the *E. coli* LacZ' sequence for codons Thr Met Ile Asn; an inserted tryptophan codon; codons 4–376 of Pfu DNA polymerase; a Ser-Gly-Asp-Leu linker; codons 240–834 of *Thermus thermophilus* HB8 DNA polymerase; followed by the stop codon TGA. This pUC18 based vector also encodes ampicillin resistance (FIG. 8).

Cells (35 g) containing the plasmid were suspended in 70 ml of buffer A (20 mM K-phosphate pH 7.0, 2mM DTT, 0.5mM EDTA) containing 0.2M NaCl and 0.1 mM PMSF. The cellular walls were disrupted with an ultrasonic disintegrator (MSE, 150 wt) at maximum amplitude for 15 minutes (30 impulses, each for 30 sec) and with cooling on ice. The suspension was then centrifuged at 40,000 g, the pellet discarded, and 5% polyethylenimine was added to the supernatant to a final concentration of 0.1%. The precipitate was separated by centrifugation, and the remaining proteins precipitated with ammonium sulfate at 45% saturation. The resulting polymerase-containing precipitate was collected by centrifugation at 20,000g and dissolved in buffer A (30 ml) containing 0.1 M NaCl and 0.2% Tween-20, heated for 15 minutes at 75° C. in the presence of 10 mM $MgCl_2$, and centrifuged for 10 minutes at 40,000 g.

The supernatant was loaded on to a (2.5×20 cm) phosphocellulose P-11 column (Whatman) equilibrated in buffer A containing 0.1 M NaCl, and washed out with the same buffer. The proteins were eluted with a linear gradient of NaCl concentrations ranging from 100 to 500 mM in buffer A. The gradient volume was 800 ml, and the flow rate was 60 ml/h. Polymerase was eluted at NaCl concentrations ranging from 280 to 330 mM.

The fractions were tested for Polymerase activity, assayed via inclusion of the radioactive-labeled nucleotide $^{32}P$ (dATP) into the acid-insoluble pellet [Myers T. W., Gelfand D. H., (1991) Biochemistry, v30, N31, p7661–7666], as in Example 4.

Fractions containing the polymerase were combined, dialyzed against buffer A containing 50 mM NaCl and loaded on to a column (0.6×6 cm) of DEAE-cellulose (Whatman) equilibrated with same buffer. The proteins were eluted with a linear gradient of NaCl concentrations ranging from 50 to 250 mM in buffer A. The gradient volume was 150 ml, and the flow rate was 15 ml/h. The polymerase was eluted at 150–200 mM NaCl.

The purified enzymes were stored at −20° C. in the following buffer: 100 mM NaCl; 10 mM Tris HCl pH 7.5; 1 mM DTT; 0.2% Tween 20 and 50% (v/v) glycerol.

Homogeneity of the polymerase preparations was not less than 95% according to SDS electrophoresis data on a 10% polyacrylamide gel (FIG. 7).

EXAMPLE 10

Polymerase Fidelity

Figure 10:
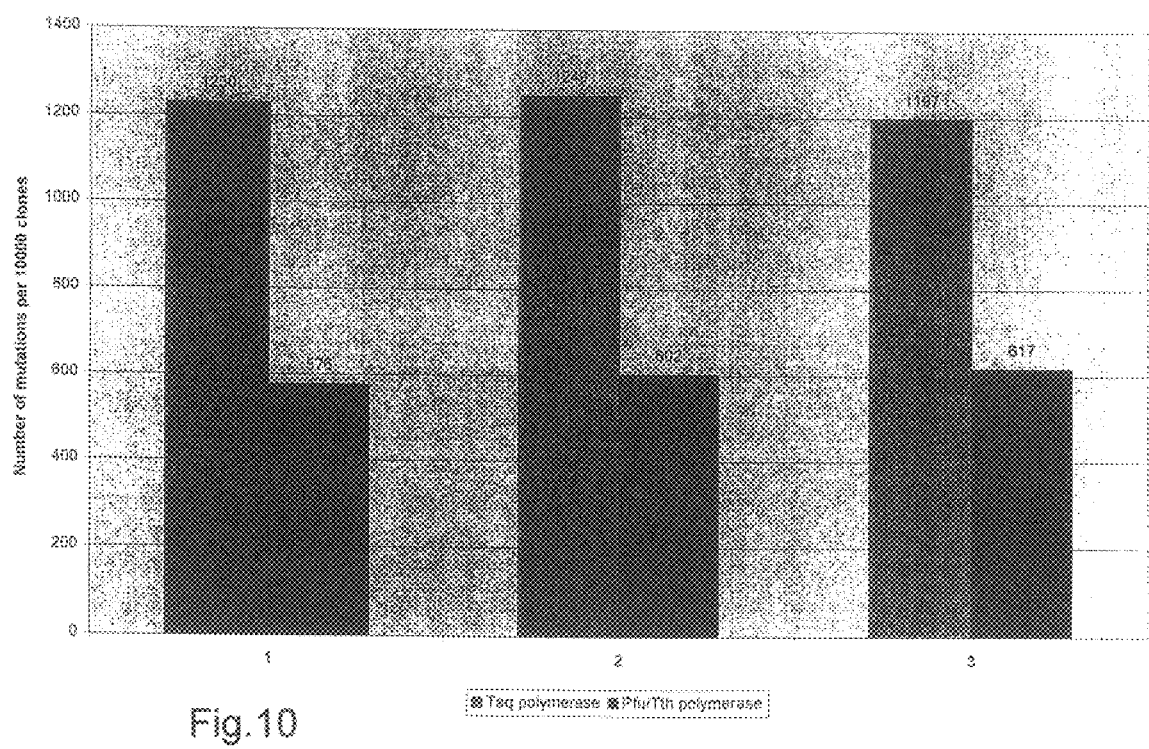
FIG. 10 shows the relative fidelity of the chimaeric Pfi/T.th enzyme in comparison to Taq DNA polymerase.

The fidelity of the chimaeric polymerase as produced in Example 9 was compared with that of Taq DNA polymerase. The fidelity was assessed using pUR222 using the method of Barnes, W. M. [(1992) Gene, 112, 29–35]. Results are shown in FIG. 10. The chimaeric enzyme had an approximately 2 fold lower relative mutation rate, when compared to full length Taq DNA polymerase.

EXAMPLE 11

DNA Amplification

λ phage DNA was amplified using the primer pairs Prλ1 and Prλ3, Prλ1 and Prλ7 or Prλ1 and Prλ8. The primer sequences were as follows:

Prλ1: 5'-GATGAGTTCGTGTCCGTACAACTGG-3'

Prλ3 5'-TTCCCAGCCACACGCTGCATGACAT-3' [SEQ ID NO 14]

Prλ7 5'-TGTTGACCTTGCCTGCAGCAACGC-3'[SEQ ID NO 15]

Prλ8 5'-TCGATCACACTCAGCAACTGCGTGG-3

The Prλ1 and Prλ3 primers are predicted to produce a product of 1270 base pairs. The Prλ1 and Prλ7 primersare predicted to produce a product of 2500 base pairs. The Prλ1 and Prλ8 primers are predicted to produce a product of 5695 base pairs.

Figure 9:
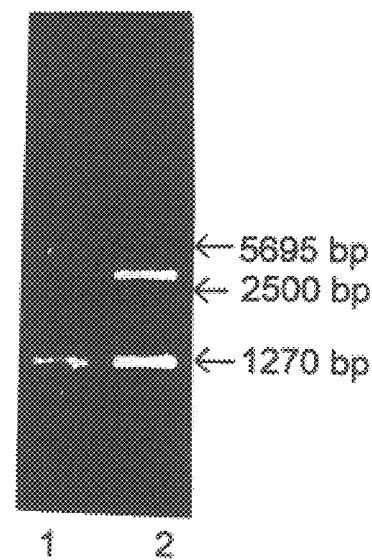
FIG. 9 is a photograph of an agarose gel, which compares the PCR amplification obtainable by Taq DNA polymerase, and the Pfu/T.th chimaeric enzyme of the invention.

Results are shown in FIG. 9, and indicate that the Pfu/T.th chimaeric enzyme is able to amplify longer fragments of DNA than Taq DNA polymerase, and to amplify more target than Taq DNA polymerase (compare the intensity of the 2500 kb band in lane 1 with lane 2).

Figures

The figures referred to in the Examples above are described more fully below.

FIG. 1

FIG. 1 shows a photograph of a 10% SDS polyacrylamide gel, run to identify plasmids which were capable of producing a protein of a size corresponding to that of the chimaeric Pfu-Taq DNA polymerase. Protein production was induced from ampicillin resistant colonies produced as in Example 3 (infra). Cell extracts were assayed for the presence of a 110–120 kDa protein. SDS was added to the cell extract to a final concentration of 0.2%, and P-mercaptoethanol to 0.1 M. After incubation for 5 minutes at 75° C., samples were loaded on a 10% SDS polyacrylamide gel. After electrophoresis, the gel was stained with Coomassie blue. The lanes are as follows:

Lane 1 Molecular weight markers. phosphorylase b, (98 kDa), BSA (68 kDa), ovalbumin (43 kDa), α-chymotrypsin (25 kDa).

Lane 2 T4 DNA polymerase (114 kDa), Taq DNA polymerase (94 kDa).

Lane 3–6 *E. coli* cell extracts after IPTG induction.

Lane 7 *E. coli* cell extract without IPTG induction.

The results identify three samples that contain protein of the expected molecular weight, in lanes 3, 5 and 6.

FIG. 2

FIG. 2 illustrates the ability of Pfu DNA polymerase, Taq DNA polymnerase and the chimaeric Pfu-Taq enzyme of the invention to amplify DNA under different conditions. Two sets of primers were used, designed to hybridize to sequences 500 bp apart on λ DNA. The primers were Prλ1 and Prλ.6. Sequences of these primers are given in Example 6 (infra). Samples of the three enzymes were heated at 95° C. for 30 minutes, and then added to a PCR reaction mix as described in Example 4. A PCR reaction of 30 cycles was run, after which the products of the PCR reaction were separated by electrophoresis on a 1.3% agarose gel. In parallel, PCR reactions were run using enzymes which were not heat treated prior to use. These products were loaded on the same gel as above. The gel was stained with ethidium bromide, and then photographed under UV light.

Lanes 1 and 2 contain DNA amplified by Pfu DNA polymerase

Lanes 3 and 4 contain DNA amplified by Taq DNA polyrnerase

Lanes 5 and 6 contain DNA amplified by the chimaeric DNA polymerase of the invention.

The enzymes used in the reactions of lanes 1, 4 and 6 were not preheated

The enzymes used in the reactions of lanes 2, 3 and 5 were preheated for 30 minutes.

The results indicate that Pfu DNA polymerase is more susceptible to heatthan either Taq DNA polymerase or the chimaeric enzyme of the invention.

FIG. 3

FIG. 3 shows the steps used in construction of plasmid pCHIE1, which contains the chimaeric DNA sequence.

FIG. 4

FIG. 4 illustrates the purity of the chimaeric Pfu-Taq DNA polymerase, at each stage of the purification process. Purity was assessed by SDS polyacrylamide gel electrophoresis. At each purification step, an aliquot of the protein sample was removed. SDS was added to the protein sample to a concentration of 0.2%, and β-mercaptoethanol to a concentration of 0.1 M. The samples were then heated to 75° C. for 5 minutes before being loaded onto a 10% SDS polyacrylamide gel. After electrophoresis the gel was stained with Coomassie blue.

Lane 1: Sample after polyethyleneimine precipitation step.

Lane 2: Sample after ammonium sulfate precipitation.

Lane 3: Sample after heating at 75° C. for 15 minutes.

Lane 4: Sample after phosphocellulose chromatography step.

Lane 5: Sample after DEAE chromatography step.

FIG. 5

FIG. 5 illustrates the fragment sizes that may be amplified by Taq DNA polymerase, Pfu DNA polymerase and the chimaeric Pfu-Taq DNA polymerase. The experiment is described in Example 6.

FIG. 6

FIG. 6 is a graph to illustrate the fidelity of the chimaeric Pfu-Taq polymerase, in comparison with Taq DNA polymerase. Details are given in Example 5.

FIG. 7

FIG. 7 shows a photograph of a 10% SDS polyacryamide gel, run to identify plasmids which were capable of producing a protein of a size corresponding to that of the chimaeric DNA polymerase. Protein production was induced from ampicillin resistant colonies produced as in Example 3 (infra). Cell extracts were assayed for the presence of a 110–120 kDa protein. SDS was added to the cell extract to a final concentration of 0.2%, and β-mercaptoethanol to 0.1M. After incubation for 5 minutes at 75° C., samples were loaded on a 10% SDS polyacrylamide gel. After electrophoresis the gel was stained with Coomassie blue. The lanes are as follows:

Lane 1 Molecular weight markers: phosphorylase b, (98 kDa), bovine serum albumin (68 kDa), ovalbumin (43 kDa), α-chymotrypsin (25 kDa).

Lane 2 Pfu-T.th chimaeric DNA polymerase

FIG. 8

FIG. 8 shows the steps used in construction of plasmid pCHIE2, which contains the chimaeric DNA sequence.

FIG. 9

FIG. 9 illustrates the ability of Taq DNA polymerase and the chimaeric Pfu-T.th enzyme of the invention to amplify DNA under different conditions. Details are given in Example 11.

FIG. 10

FIG. 10 is a graph to illustrate the fidelity of the chimaeric polymerase, in comparison with Taq DNA polymerase. Details are given in Example 10.

What is claimed is:

1. A chimaeric enzyme containing a proof-reading function derived from an enzyme of one species and a polymerase function derived from an enzyme of a different species, wherein said chimaeric enzyme is thermostable, wherein the chimaeric enzyme comprises amino acids 4–376 of *Pyrococcus furriosus* DNA polymerase I and amino acids 238–832 of *Thermus aquaticus* DNA polymerase I, wherein said chimaeric enzyme comprises the sequence given in SEQ ID No. 1.

2. A chimaeric enzyme containing a proof-reading function derived from an enzyme of one species and a polymerase function derived from an enzyme of a different species, wherein said chimaeric enzyme is thermostable, wherein the chimaeric enzyme comprises amino acids 4–376 of *Pyrococcus furiosus* DNA polymerase I and amino acids 240–834 of *Thermus thermophilus* DNA polymerase I, wherein said chimaeric enzyme comprises the sequence given in SEQ ID No. 2.

3. A kit containing the chimareic enzyme of claim 1 or claim 2 in combination with other reagents, suitable for use in laboratory experiments.

* * * * *

SEQUENCE LISTING

<160> NUMBER OF SEQ ID NOS: 15

<210> SEQ ID NO 1
<211> LENGTH: 980
<212> TYPE: PRT
<213> ORGANISM: Pyrococcus furiosus/Thermus aquaticus

<400> SEQUENCE: 1

```
Met Thr Met Ile Thr Asn Trp Asp Val Asp Tyr Ile Thr Glu Glu Gly
 1               5                  10                  15

Lys Pro Val Ile Arg Leu Phe Lys Glu Asn Gly Lys Phe Lys Ile
            20                  25                  30

Glu His Asp Arg Thr Phe Arg Pro Tyr Ile Tyr Ala Leu Leu Arg Asp
        35                  40                  45

Asp Ser Lys Ile Glu Glu Val Lys Lys Ile Thr Gly Glu Arg His Gly
    50                  55                  60

Lys Ile Val Arg Ile Val Asp Val Glu Lys Val Glu Lys Lys Phe Leu
65                  70                  75                  80

Gly Lys Pro Ile Thr Val Trp Lys Leu Tyr Leu Glu His Pro Gln Asp
                85                  90                  95

Val Pro Thr Ile Arg Glu Lys Val Arg Glu His Pro Ala Val Val Asp
            100                 105                 110

Ile Phe Glu Tyr Asp Ile Pro Phe Ala Lys Arg Tyr Leu Ile Asp Lys
        115                 120                 125

Gly Leu Ile Pro Met Glu Gly Glu Glu Leu Lys Ile Leu Ala Phe
    130                 135                 140

Asp Ile Glu Thr Leu Tyr His Glu Gly Glu Glu Phe Gly Lys Gly Pro
145                 150                 155                 160

Ile Ile Met Ile Ser Tyr Ala Asp Glu Asn Glu Ala Lys Val Ile Thr
                165                 170                 175

Trp Lys Asn Ile Asp Leu Pro Tyr Val Glu Val Val Ser Ser Glu Arg
            180                 185                 190

Glu Met Ile Lys Arg Phe Leu Arg Ile Ile Arg Glu Lys Asp Pro Asp
        195                 200                 205

Ile Ile Val Thr Tyr Asn Gly Asp Ser Phe Asp Phe Pro Tyr Leu Ala
    210                 215                 220

Lys Arg Ala Glu Lys Leu Gly Ile Lys Leu Thr Ile Gly Arg Asp Gly
225                 230                 235                 240

Ser Glu Pro Lys Met Gln Arg Ile Gly Asp Met Thr Ala Val Glu Val
                245                 250                 255

Lys Gly Arg Ile His Phe Asp Leu Tyr His Val Ile Thr Arg Thr Ile
            260                 265                 270

Asn Leu Pro Thr Tyr Thr Leu Glu Ala Val Tyr Glu Ala Ile Phe Gly
        275                 280                 285

Lys Pro Lys Glu Lys Val Tyr Ala Asp Glu Ile Ala Lys Ala Trp Glu
    290                 295                 300
```

-continued

```
Ser Gly Glu Asn Leu Glu Arg Val Ala Lys Tyr Ser Met Glu Asp Ala
305                 310                 315                 320

Lys Ala Thr Tyr Glu Leu Gly Lys Glu Phe Leu Pro Met Glu Ile Gln
            325                 330                 335

Leu Ser Arg Leu Val Gly Gln Pro Leu Trp Asp Val Ser Arg Ser Ser
            340                 345                 350

Thr Gly Asn Leu Val Glu Trp Phe Leu Leu Arg Lys Ala Tyr Glu Arg
            355                 360                 365

Asn Glu Val Ala Pro Asn Lys Pro Ser Glu Glu Ser Gly Asp Leu
370                 375                 380

Asp Asp Leu Lys Leu Ser Trp Asp Leu Ala Lys Val Arg Thr Asp Leu
385                 390                 395                 400

Pro Leu Glu Val Asp Phe Ala Lys Arg Arg Glu Pro Asp Arg Glu Arg
            405                 410                 415

Leu Arg Ala Phe Leu Glu Arg Leu Glu Phe Gly Ser Leu Leu His Glu
            420                 425                 430

Phe Gly Leu Leu Glu Ser Pro Lys Ala Leu Glu Ala Pro Trp Pro
            435                 440                 445

Pro Pro Glu Gly Ala Phe Val Gly Phe Val Leu Ser Arg Lys Glu Pro
450                 455                 460

Met Trp Ala Asp Leu Leu Ala Leu Ala Ala Arg Gly Gly Arg Val
465                 470                 475                 480

His Arg Ala Pro Glu Pro Tyr Lys Ala Leu Arg Asp Leu Lys Glu Ala
            485                 490                 495

Arg Gly Leu Leu Ala Lys Asp Leu Ser Val Leu Ala Leu Arg Glu Gly
            500                 505                 510

Leu Gly Leu Pro Pro Gly Asp Asp Pro Met Leu Leu Ala Tyr Leu Leu
            515                 520                 525

Asp Pro Ser Asn Thr Thr Pro Glu Gly Val Ala Arg Arg Tyr Gly Gly
            530                 535                 540

Glu Trp Thr Glu Glu Ala Gly Glu Arg Ala Ala Leu Ser Glu Arg Leu
545                 550                 555                 560

Phe Ala Asn Leu Trp Gly Arg Leu Glu Gly Glu Glu Arg Leu Leu Trp
            565                 570                 575

Leu Tyr Arg Glu Val Glu Arg Pro Leu Ser Ala Val Leu Ala His Met
            580                 585                 590

Glu Ala Thr Gly Val Arg Leu Asp Val Ala Tyr Leu Arg Ala Leu Ser
            595                 600                 605

Leu Glu Val Ala Glu Glu Ile Ala Arg Leu Glu Ala Glu Val Phe Arg
            610                 615                 620

Leu Ala Gly His Pro Phe Asn Leu Asn Ser Arg Asp Gln Leu Glu Arg
625                 630                 635                 640

Val Leu Phe Asp Glu Leu Gly Leu Pro Ala Ile Gly Lys Thr Glu Lys
            645                 650                 655

Thr Gly Lys Arg Ser Thr Ser Ala Ala Val Leu Asp Ala Leu Arg Glu
            660                 665                 670

Ala His Pro Ile Val Glu Lys Ile Leu Gln Tyr Arg Glu Leu Thr Lys
            675                 680                 685

Leu Lys Ser Thr Tyr Ile Asp Pro Leu Pro Asp Leu Ile His Pro Arg
            690                 695                 700

Thr Gly Arg Leu His Thr Arg Phe Asn Gln Thr Ala Thr Ala Thr Gly
705                 710                 715                 720
```

-continued

```
Arg Leu Ser Ser Ser Asp Pro Asn Leu Gln Asn Ile Pro Val Arg Thr
            725                 730                 735

Pro Leu Gly Gln Arg Ile Arg Arg Ala Phe Ile Ala Glu Glu Gly Trp
            740                 745                 750

Leu Leu Met Ala Leu Asp Tyr Ser Gln Ile Glu Leu Arg Val Leu Ala
            755                 760                 765

His Leu Ser Gly Asp Glu Asn Leu Ile Arg Val Phe Gln Glu Gly Arg
            770                 775                 780

Asp Ile His Thr Glu Thr Ala Ser Trp Met Phe Gly Val Pro Arg Glu
785                 790                 795                 800

Ala Val Asp Pro Leu Met Arg Arg Ala Ala Lys Thr Ile Asn Phe Gly
            805                 810                 815

Val Leu Tyr Gly Met Ser Ala His Arg Leu Ser Gln Glu Leu Ala Ile
            820                 825                 830

Pro Tyr Glu Glu Ala Gln Ala Phe Ile Glu Arg Tyr Phe Gln Ser Phe
            835                 840                 845

Pro Lys Val Arg Ala Trp Ile Glu Lys Thr Leu Glu Glu Gly Arg Arg
            850                 855                 860

Arg Gly Tyr Val Glu Thr Leu Phe Gly Arg Arg Arg Tyr Val Pro Asp
865                 870                 875                 880

Leu Glu Ala Arg Val Lys Ser Val Arg Glu Ala Ala Glu Arg Met Ala
            885                 890                 895

Phe Asn Met Pro Val Gln Gly Thr Ala Ala Asp Leu Met Lys Leu Ala
            900                 905                 910

Met Val Lys Leu Phe Pro Arg Leu Glu Glu Met Gly Ala Arg Met Leu
            915                 920                 925

Leu Gln Val His Asp Glu Leu Val Leu Glu Ala Pro Lys Glu Arg Ala
            930                 935                 940

Glu Ala Val Ala Arg Leu Ala Lys Glu Val Met Glu Gly Val Tyr Pro
945                 950                 955                 960

Leu Ala Val Pro Leu Glu Val Glu Val Gly Ile Gly Glu Asp Trp Leu
            965                 970                 975

Ser Ala Lys Glu
            980

<210> SEQ ID NO 2
<211> LENGTH: 980
<212> TYPE: PRT
<213> ORGANISM: Thermus thermophilus/Pyrococcus furiosus

<400> SEQUENCE: 2

Met Thr Met Ile Thr Asn Trp Asp Val Asp Tyr Ile Thr Glu Glu Gly
  1               5                  10                  15

Lys Pro Val Ile Arg Leu Phe Lys Lys Glu Asn Gly Lys Phe Lys Ile
             20                  25                  30

Glu His Asp Arg Thr Phe Arg Pro Tyr Ile Tyr Ala Leu Leu Arg Asp
         35                  40                  45

Asp Ser Lys Ile Glu Glu Val Lys Lys Ile Thr Gly Glu Arg His Gly
     50                  55                  60

Lys Ile Val Arg Ile Val Asp Val Glu Lys Val Glu Lys Phe Leu
 65                  70                  75                  80

Gly Lys Pro Ile Thr Val Trp Lys Leu Tyr Leu Glu His Pro Gln Asp
             85                  90                  95

Val Pro Thr Ile Arg Glu Lys Val Arg Glu His Pro Ala Val Val Asp
            100                 105                 110
```

```
Ile Phe Glu Tyr Asp Ile Pro Phe Ala Lys Arg Tyr Leu Ile Asp Lys
        115                 120                 125

Gly Leu Ile Pro Met Glu Gly Glu Glu Leu Lys Ile Leu Ala Phe
    130                 135                 140

Asp Ile Glu Thr Leu Tyr His Glu Gly Glu Phe Gly Lys Gly Pro
145                 150                 155                 160

Ile Ile Met Ile Ser Tyr Ala Asp Glu Asn Glu Ala Lys Val Ile Thr
                165                 170                 175

Trp Lys Asn Ile Asp Leu Pro Tyr Val Glu Val Val Ser Ser Glu Arg
            180                 185                 190

Glu Met Ile Lys Arg Phe Leu Arg Ile Ile Arg Glu Lys Asp Pro Asp
        195                 200                 205

Ile Ile Val Thr Tyr Asn Gly Asp Ser Phe Asp Phe Pro Tyr Leu Ala
210                 215                 220

Lys Arg Ala Glu Lys Leu Gly Ile Lys Leu Thr Ile Gly Arg Asp Gly
225                 230                 235                 240

Ser Glu Pro Lys Met Gln Arg Ile Gly Asp Met Thr Ala Val Glu Val
                245                 250                 255

Lys Gly Arg Ile His Phe Asp Leu Tyr His Val Ile Thr Arg Thr Ile
            260                 265                 270

Asn Leu Pro Thr Tyr Thr Leu Glu Ala Val Tyr Glu Ala Ile Phe Gly
        275                 280                 285

Lys Pro Lys Glu Lys Val Tyr Ala Asp Glu Ile Ala Lys Ala Trp Glu
    290                 295                 300

Ser Gly Glu Asn Leu Glu Arg Val Ala Lys Tyr Ser Met Glu Asp Ala
305                 310                 315                 320

Lys Ala Thr Tyr Glu Leu Gly Lys Glu Phe Leu Pro Met Glu Ile Gln
                325                 330                 335

Leu Ser Arg Leu Val Gly Gln Pro Leu Trp Asp Val Ser Arg Ser Ser
            340                 345                 350

Thr Gly Asn Leu Val Glu Trp Phe Leu Leu Arg Lys Ala Tyr Glu Arg
        355                 360                 365

Asn Glu Val Ala Pro Asn Lys Pro Ser Glu Glu Ser Gly Asp Leu
    370                 375                 380

Asp Asp Leu Arg Leu Ser Leu Glu Leu Ser Arg Val Arg Thr Asp Leu
385                 390                 395                 400

Pro Leu Glu Val Asp Leu Ala Gln Gly Arg Glu Pro Asp Arg Glu Gly
                405                 410                 415

Leu Arg Ala Phe Leu Glu Arg Leu Glu Phe Gly Ser Leu Leu His Glu
            420                 425                 430

Phe Gly Leu Leu Glu Ala Pro Ala Pro Leu Glu Glu Ala Pro Trp Pro
        435                 440                 445

Pro Pro Glu Gly Ala Phe Val Gly Phe Val Leu Ser Arg Pro Glu Pro
    450                 455                 460

Met Trp Ala Glu Leu Lys Ala Leu Ala Ala Cys Arg Asp Gly Arg Val
465                 470                 475                 480

His Arg Ala Ala Asp Pro Leu Ala Gly Leu Lys Asp Leu Lys Glu Val
                485                 490                 495

Arg Gly Leu Leu Ala Lys Asp Leu Ala Val Leu Ala Ser Arg Glu Gly
            500                 505                 510

Leu Asp Leu Val Pro Gly Asp Asp Pro Met Leu Leu Ala Tyr Leu Leu
        515                 520                 525
```

-continued

```
Asp Pro Ser Asn Thr Thr Pro Glu Gly Val Ala Arg Arg Tyr Gly Gly
            530                 535                 540

Glu Trp Thr Glu Asp Ala Ala His Arg Ala Leu Leu Ser Glu Arg Leu
545                 550                 555                 560

His Arg Asn Leu Leu Lys Arg Leu Glu Gly Glu Lys Leu Leu Trp
                565                 570                 575

Leu Tyr His Glu Val Glu Lys Pro Leu Ser Arg Val Leu Ala His Met
            580                 585                 590

Glu Ala Thr Gly Val Arg Leu Asp Val Ala Tyr Leu Gln Ala Leu Ser
                595                 600                 605

Leu Glu Leu Ala Glu Glu Ile Arg Arg Leu Glu Glu Val Phe Arg
            610                 615                 620

Leu Ala Gly His Pro Phe Asn Leu Asn Ser Arg Asp Gln Leu Glu Arg
625                 630                 635                 640

Val Leu Phe Asp Glu Leu Arg Leu Pro Ala Leu Gly Lys Thr Gln Lys
                645                 650                 655

Thr Gly Lys Arg Ser Thr Ser Ala Ala Val Leu Glu Ala Leu Arg Glu
                660                 665                 670

Ala His Pro Ile Val Glu Lys Ile Leu Gln His Arg Glu Leu Thr Lys
            675                 680                 685

Leu Lys Asn Thr Tyr Val Asp Pro Leu Pro Ser Leu Val His Pro Arg
            690                 695                 700

Thr Gly Arg Leu His Thr Arg Phe Asn Gln Thr Ala Thr Ala Thr Gly
705                 710                 715                 720

Arg Leu Ser Ser Ser Asp Pro Asn Leu Gln Asn Ile Pro Val Arg Thr
                725                 730                 735

Pro Leu Gly Gln Arg Ile Arg Arg Ala Phe Val Ala Glu Ala Gly Trp
                740                 745                 750

Ala Leu Val Ala Leu Asp Tyr Ser Gln Ile Glu Leu Arg Val Leu Ala
            755                 760                 765

His Leu Ser Gly Asp Glu Asn Leu Ile Arg Val Phe Gln Glu Gly Lys
            770                 775                 780

Asp Ile His Thr Gln Thr Ala Ser Trp Met Phe Gly Val Pro Pro Glu
785                 790                 795                 800

Ala Val Asp Pro Leu Met Arg Arg Ala Ala Lys Thr Val Asn Phe Gly
                805                 810                 815

Val Leu Tyr Gly Met Ser Ala His Arg Leu Ser Gln Glu Leu Ala Ile
                820                 825                 830

Pro Tyr Glu Glu Ala Val Ala Phe Ile Glu Arg Tyr Phe Gln Ser Phe
            835                 840                 845

Pro Lys Val Arg Ala Trp Ile Glu Lys Thr Leu Glu Glu Gly Arg Lys
            850                 855                 860

Arg Gly Tyr Val Glu Thr Leu Phe Gly Arg Arg Arg Tyr Val Pro Asp
865                 870                 875                 880

Leu Asn Ala Arg Val Lys Ser Val Arg Glu Ala Ala Glu Arg Met Ala
                885                 890                 895

Phe Asn Met Pro Val Gln Gly Thr Ala Ala Asp Leu Met Lys Leu Ala
            900                 905                 910

Met Val Lys Leu Phe Pro Arg Leu Arg Glu Met Gly Ala Arg Met Leu
            915                 920                 925

Leu Gln Val His Asp Glu Leu Leu Leu Glu Ala Pro Gln Ala Arg Ala
            930                 935                 940

Glu Glu Val Ala Ala Leu Ala Lys Glu Ala Met Glu Lys Ala Tyr Pro
```

-continued

```
                945            950           955           960
                Leu Ala Val Pro Leu Glu Val Glu Val Gly Met Gly Glu Asp Trp Leu
                                    965           970           975
                Ser Ala Lys Gly
                            980

<210> SEQ ID NO 3
<211> LENGTH: 2943
<212> TYPE: DNA
<213> ORGANISM: Pyrococcus furiosus/Thermus aquaticus
<220> FEATURE:
<221> NAME/KEY: CDS
<222> LOCATION: (1)..(2943)

<400> SEQUENCE: 3 atg acc atg att acg aat tgg gat gtg gat tac ata act gaa gaa gga        48
Met Thr Met Ile Thr Asn Trp Asp Val Asp Tyr Ile Thr Glu Glu Gly
  1               5                  10                  15 aaa cct gtt att agg cta ttc aaa aaa gag aac gga aaa ttt aag ata        96
Lys Pro Val Ile Arg Leu Phe Lys Lys Glu Asn Gly Lys Phe Lys Ile
             20                  25                  30 gag cat gat aga act ttt aga cca tac att tac gct ctt ctc agg gat       144
Glu His Asp Arg Thr Phe Arg Pro Tyr Ile Tyr Ala Leu Leu Arg Asp
         35                  40                  45 gat tca aag att gaa gaa gtt aag aaa ata acg ggg gaa agg cat gga       192
Asp Ser Lys Ile Glu Glu Val Lys Lys Ile Thr Gly Glu Arg His Gly
     50                  55                  60 aag att gtg aga att gtt gat gta gag aag gtt gag aaa aag ttt ctc       240
Lys Ile Val Arg Ile Val Asp Val Glu Lys Val Glu Lys Lys Phe Leu
 65                  70                  75                  80 ggc aag cct att acc gtg tgg aaa ctt tat ttg gaa cat ccc caa gat       288
Gly Lys Pro Ile Thr Val Trp Lys Leu Tyr Leu Glu His Pro Gln Asp
                 85                  90                  95 gtt ccc act att aga gaa aaa gtt aga gaa cat cca gca gtt gtg gac       336
Val Pro Thr Ile Arg Glu Lys Val Arg Glu His Pro Ala Val Val Asp
            100                 105                 110 atc ttc gaa tac gat att cca ttt gca aag aga tac ctc atc gac aaa       384
Ile Phe Glu Tyr Asp Ile Pro Phe Ala Lys Arg Tyr Leu Ile Asp Lys
        115                 120                 125 ggc cta ata cca atg gag ggg gaa gaa gag cta aag att ctt gcc ttc       432
Gly Leu Ile Pro Met Glu Gly Glu Glu Glu Leu Lys Ile Leu Ala Phe
    130                 135                 140 gat ata gaa acc ctc tat cac gaa gga gaa gag ttt gga aaa ggc cca       480
Asp Ile Glu Thr Leu Tyr His Glu Gly Glu Glu Phe Gly Lys Gly Pro
145                 150                 155                 160 att ata atg att agt tat gca gat gaa aat gaa gca aag gtg att act       528
Ile Ile Met Ile Ser Tyr Ala Asp Glu Asn Glu Ala Lys Val Ile Thr
                165                 170                 175 tgg aaa aac ata gat ctt cca tac gtt gag gtt gta tca agc gag aga       576
Trp Lys Asn Ile Asp Leu Pro Tyr Val Glu Val Val Ser Ser Glu Arg
            180                 185                 190 gag atg ata aag aga ttt ctc agg att atc agg gag aag gat cct gac       624
Glu Met Ile Lys Arg Phe Leu Arg Ile Ile Arg Glu Lys Asp Pro Asp
        195                 200                 205 att ata gtt act tat aat gga gac tca ttc gac ttc cca tat tta gcg       672
Ile Ile Val Thr Tyr Asn Gly Asp Ser Phe Asp Phe Pro Tyr Leu Ala
    210                 215                 220 aaa agg gca gaa aaa ctt ggg att aaa tta acc att gga aga gat gga       720
Lys Arg Ala Glu Lys Leu Gly Ile Lys Leu Thr Ile Gly Arg Asp Gly
225                 230                 235                 240
```

```
agc gag ccc aag atg cag aga ata ggc gat atg acg gct gta gaa gtc      768
Ser Glu Pro Lys Met Gln Arg Ile Gly Asp Met Thr Ala Val Glu Val
            245                 250                 255 aag gga aga ata cat ttc gac ttg tat cat gta ata aca agg aca ata      816
Lys Gly Arg Ile His Phe Asp Leu Tyr His Val Ile Thr Arg Thr Ile
        260                 265                 270 aat ctc cca aca tac aca cta gag gct gta tat gaa gca att ttt gga      864
Asn Leu Pro Thr Tyr Thr Leu Glu Ala Val Tyr Glu Ala Ile Phe Gly
            275                 280                 285 aag cca aag gag aag gta tac gcc gac gag ata gca aaa gcc tgg gaa      912
Lys Pro Lys Glu Lys Val Tyr Ala Asp Glu Ile Ala Lys Ala Trp Glu
        290                 295                 300 agt gga gag aac ctt gag aga gtt gcc aaa tac tcg atg gaa gat gca      960
Ser Gly Glu Asn Leu Glu Arg Val Ala Lys Tyr Ser Met Glu Asp Ala
305                 310                 315                 320 aag gca act tat gaa ctc ggg aaa gaa ttc ctt cca atg gaa att cag     1008
Lys Ala Thr Tyr Glu Leu Gly Lys Glu Phe Leu Pro Met Glu Ile Gln
            325                 330                 335 ctt tca aga tta gtt gga caa cct tta tgg gat gtt tca agg tca agc     1056
Leu Ser Arg Leu Val Gly Gln Pro Leu Trp Asp Val Ser Arg Ser Ser
        340                 345                 350 aca ggg aac ctt gta gag tgg ttc tta ctt agg aaa gcc tac gaa aga     1104
Thr Gly Asn Leu Val Glu Trp Phe Leu Leu Arg Lys Ala Tyr Glu Arg
            355                 360                 365 aac gaa gta gct cca aac aag cca agt gaa gag gag tcc ggg gat ctg     1152
Asn Glu Val Ala Pro Asn Lys Pro Ser Glu Glu Glu Ser Gly Asp Leu
        370                 375                 380 gac gat ctg aag ctc tcc tgg gac ctg gcc aag gtg cgc acc gac ctg     1200
Asp Asp Leu Lys Leu Ser Trp Asp Leu Ala Lys Val Arg Thr Asp Leu
385                 390                 395                 400 ccc ctg gag gtg gac ttc gcc aaa agg cgg gag ccc gac cgg gag agg     1248
Pro Leu Glu Val Asp Phe Ala Lys Arg Arg Glu Pro Asp Arg Glu Arg
            405                 410                 415 ctt agg gcc ttt ctg gag agg ctt gag ttt ggc agc ctc ctc cac gag     1296
Leu Arg Ala Phe Leu Glu Arg Leu Glu Phe Gly Ser Leu Leu His Glu
        420                 425                 430 ttc ggc ctt ctg gaa agc ccc aag gcc ctg gag gag gcc ccc tgg ccc     1344
Phe Gly Leu Leu Glu Ser Pro Lys Ala Leu Glu Glu Ala Pro Trp Pro
            435                 440                 445 ccg ccg gaa ggg gcc ttc gtg ggc ttt gtg ctt tcc cgc aag gag ccc     1392
Pro Pro Glu Gly Ala Phe Val Gly Phe Val Leu Ser Arg Lys Glu Pro
        450                 455                 460 atg tgg gcc gat ctt ctg gcc ctg gcc gcc gcc agg ggg ggc cgg gtc     1440
Met Trp Ala Asp Leu Leu Ala Leu Ala Ala Ala Arg Gly Gly Arg Val
465                 470                 475                 480 cac cgg gcc ccc gag cct tat aaa gcc ctc agg gac ctg aag gag gcg     1488
His Arg Ala Pro Glu Pro Tyr Lys Ala Leu Arg Asp Leu Lys Glu Ala
            485                 490                 495 cgg ggg ctt ctc gcc aaa gac ctg agc gtt ctg gcc ctg agg gaa ggc     1536
Arg Gly Leu Leu Ala Lys Asp Leu Ser Val Leu Ala Leu Arg Glu Gly
        500                 505                 510 ctt ggc ctc ccg ccc ggc gac gac ccc atg ctc ctc gcc tac ctc ctg     1584
Leu Gly Leu Pro Pro Gly Asp Asp Pro Met Leu Leu Ala Tyr Leu Leu
            515                 520                 525 gac cct tcc aac acc acc ccc gag ggg gtg gcc cgg cgc tac ggc ggg     1632
Asp Pro Ser Asn Thr Thr Pro Glu Gly Val Ala Arg Arg Tyr Gly Gly
530                 535                 540 gag tgg acg gag gag gcg ggg gag cgg gcc gcc ctt tcc gag agg ctc     1680
Glu Trp Thr Glu Glu Ala Gly Glu Arg Ala Ala Leu Ser Glu Arg Leu
545                 550                 555                 560
```

```
ttc gcc aac ctg tgg ggg agg ctt gag ggg gag gag agg ctc ctt tgg       1728
Phe Ala Asn Leu Trp Gly Arg Leu Glu Gly Glu Glu Arg Leu Leu Trp
                565                 570                 575 ctt tac cgg gag gtg gag agg ccc ctt tcc gct gtc ctg gcc cac atg       1776
Leu Tyr Arg Glu Val Glu Arg Pro Leu Ser Ala Val Leu Ala His Met
                580                 585                 590 gag gcc acg ggg gtg cgc ctg gac gtg gcc tat ctc agg gcc ttg tcc       1824
Glu Ala Thr Gly Val Arg Leu Asp Val Ala Tyr Leu Arg Ala Leu Ser
            595                 600                 605 ctg gag gtg gcc gag gag atc gcc cgc ctc gag gcc gag gtc ttc cgc       1872
Leu Glu Val Ala Glu Glu Ile Ala Arg Leu Glu Ala Glu Val Phe Arg
        610                 615                 620 ctg gcc ggc cac ccc ttc aac ctc aac tcc cgg gac cag ctg gaa agg       1920
Leu Ala Gly His Pro Phe Asn Leu Asn Ser Arg Asp Gln Leu Glu Arg
625                 630                 635                 640 gtc ctc ttt gac gag cta ggg ctt ccc gcc atc ggc aag acg gag aag       1968
Val Leu Phe Asp Glu Leu Gly Leu Pro Ala Ile Gly Lys Thr Glu Lys
                645                 650                 655 acc ggc aag cgc tcc acc agc gcc gcc gtc ctg gac gcc ctc cgc gag       2016
Thr Gly Lys Arg Ser Thr Ser Ala Ala Val Leu Asp Ala Leu Arg Glu
                660                 665                 670 gcc cac ccc atc gtg gag aag atc ctg cag tac cgg gag ctc acc aag       2064
Ala His Pro Ile Val Glu Lys Ile Leu Gln Tyr Arg Glu Leu Thr Lys
            675                 680                 685 ctg aag agc acc tac att gac ccc ttg ccg gac ctc atc cac ccc agg       2112
Leu Lys Ser Thr Tyr Ile Asp Pro Leu Pro Asp Leu Ile His Pro Arg
        690                 695                 700 acg ggc cgc ctc cac acc cgc ttc aac cag acg gcc acg gcc acg ggc       2160
Thr Gly Arg Leu His Thr Arg Phe Asn Gln Thr Ala Thr Ala Thr Gly
705                 710                 715                 720 agg cta agt agc tcc gat ccc aac ctc cag aac atc ccc gtc cgc acc       2208
Arg Leu Ser Ser Ser Asp Pro Asn Leu Gln Asn Ile Pro Val Arg Thr
                725                 730                 735 ccg ctt ggg cag agg atc cgc cgg gcc ttc atc gcc gag gag ggg tgg       2256
Pro Leu Gly Gln Arg Ile Arg Arg Ala Phe Ile Ala Glu Glu Gly Trp
                740                 745                 750 cta ttg atg gcc ctg gac tat agc cag ata gag ctc agg gtg ctg gcc       2304
Leu Leu Met Ala Leu Asp Tyr Ser Gln Ile Glu Leu Arg Val Leu Ala
            755                 760                 765 cac ctc tcc ggc gac gag aac ctg atc cgg gtc ttc cag gag ggg cgg       2352
His Leu Ser Gly Asp Glu Asn Leu Ile Arg Val Phe Gln Glu Gly Arg
        770                 775                 780 gac atc cac acg gag acc gcc agc tgg atg ttc ggc gtc ccc cgg gag       2400
Asp Ile His Thr Glu Thr Ala Ser Trp Met Phe Gly Val Pro Arg Glu
785                 790                 795                 800 gcc gtg gac ccc ctg atg cgc cgg gcg gcc aag acc atc aac ttc ggg       2448
Ala Val Asp Pro Leu Met Arg Arg Ala Ala Lys Thr Ile Asn Phe Gly
                805                 810                 815 gtc ctc tac ggc atg tcg gcc cac cgc ctc tcc cag gag cta gcc atc       2496
Val Leu Tyr Gly Met Ser Ala His Arg Leu Ser Gln Glu Leu Ala Ile
                820                 825                 830 cct tac gag gag gcc cag gcc ttc att gag cgc tac ttt cag agc ttc       2544
Pro Tyr Glu Glu Ala Gln Ala Phe Ile Glu Arg Tyr Phe Gln Ser Phe
            835                 840                 845 ccc aag gtg cgg gcc tgg att gag aag acc ctg gag gag ggc agg agg       2592
Pro Lys Val Arg Ala Trp Ile Glu Lys Thr Leu Glu Glu Gly Arg Arg
850                 855                 860 cgg ggg tac gtg gag acc ctc ttc ggc cgc cgc cgc tac gtg cca gac       2640
Arg Gly Tyr Val Glu Thr Leu Phe Gly Arg Arg Arg Tyr Val Pro Asp
```

```
                865                 870                 875                 880
cta gag gcc cgg gtg aag agc gtg cgg gag gcg gcc gag cgc atg gcc       2688
Leu Glu Ala Arg Val Lys Ser Val Arg Glu Ala Ala Glu Arg Met Ala
                        885                 890                 895 ttc aac atg ccc gtc cag ggc acc gcc gcc gac ctc atg aag ctg gct       2736
Phe Asn Met Pro Val Gln Gly Thr Ala Ala Asp Leu Met Lys Leu Ala
                900                 905                 910 atg gtg aag ctc ttc ccc agg ctg gag gaa atg ggg gcc agg atg ctc       2784
Met Val Lys Leu Phe Pro Arg Leu Glu Glu Met Gly Ala Arg Met Leu
            915                 920                 925 ctt cag gtc cac gac gag ctg gtc ctc gag gcc cca aaa gag agg gcg       2832
Leu Gln Val His Asp Glu Leu Val Leu Glu Ala Pro Lys Glu Arg Ala
        930                 935                 940 gag gcc gtg gcc cgg ctg gcc aag gag gtc atg gag ggg gtg tat ccc       2880
Glu Ala Val Ala Arg Leu Ala Lys Glu Val Met Glu Gly Val Tyr Pro
945                 950                 955                 960 ctg gcc gtg ccc ctg gag gtg gag gtg ggg ata ggg gag gac tgg ctc       2928
Leu Ala Val Pro Leu Glu Val Glu Val Gly Ile Gly Glu Asp Trp Leu
                965                 970                 975 tcc gcc aag gag tga                                                   2943
Ser Ala Lys Glu
            980

<210> SEQ ID NO 4

<211> LENGTH: 2943
<212> TYPE: DNA
<213> ORGANISM: Thermus thermophilus /Pyrococcus furiosus
<220> FEATUR     E:
<221> NAME/KEY: CDS
<222> LOCATION: (1)..(2943)

<400> SEQUENCE: 4 atg acc atg att acg aat tgg gat gtg gat tac ata act gaa gaa gga        48
Met Thr Met Ile Thr Asn Trp Asp Val Asp Tyr Ile Thr Glu Glu Gly
 1               5                  10                  15 aaa cct gtt att agg cta ttc aaa aaa gag aac gga aaa ttt aag ata        96
Lys Pro Val Ile Arg Leu Phe Lys Lys Glu Asn Gly Lys Phe Lys Ile
                20                  25                  30 gag cat gat aga act ttt aga cca tac att tac gct ctt ctc agg gat       144
Glu His Asp Arg Thr Phe Arg Pro Tyr Ile Tyr Ala Leu Leu Arg Asp
            35                  40                  45 gat tca aag att gaa gaa gtt aag aaa ata acg ggg gaa agg cat gga       192
Asp Ser Lys Ile Glu Glu Val Lys Lys Ile Thr Gly Glu Arg His Gly
        50                  55                  60 aag att gtg aga att gtt gat gta gag aag gtt gag aaa aag ttt ctc       240
Lys Ile Val Arg Ile Val Asp Val Glu Lys Val Glu Lys Lys Phe Leu
 65                 70                  75                  80 ggc aag cct att acc gtg tgg aaa ctt tat ttg gaa cat ccc caa gat       288
Gly Lys Pro Ile Thr Val Trp Lys Leu Tyr Leu Glu His Pro Gln Asp
                85                  90                  95
gtt ccc act att aga gaa aaa gtt aga gaa cat cca gca gtt gtg gac       336
Val Pro Thr Ile Arg Glu Lys Val Arg Glu His Pro Ala Val Val Asp
            100                 105                 110 atc ttc gaa tac gat att cca ttt gca aag aga tac ctc atc gac aaa       384
Ile Phe Glu Tyr Asp Ile Pro Phe Ala Lys Arg Tyr Leu Ile Asp Lys
        115                 120                 125 ggc cta ata cca atg gag ggg gaa gaa gag cta aag att ctt gcc ttc       432
Gly Leu Ile Pro Met Glu Gly Glu Glu Glu Leu Lys Ile Leu Ala Phe
    130                 135                 140 gat ata gaa acc ctc tat cac gaa gga gaa gag ttt gga aaa ggc cca       480
```

```
Asp Ile Glu Thr Leu Tyr His Glu Gly Glu Glu Phe Gly Lys Gly Pro
145                 150                 155                 160 att ata atg att agt tat gca gat gaa aat gaa gca aag gtg att act        528
Ile Ile Met Ile Ser Tyr Ala Asp Glu Asn Glu Ala Lys Val Ile Thr
                165                 170                 175 tgg aaa aac ata gat ctt cca tac gtt gag gtt gta tca agc gag aga        576
Trp Lys Asn Ile Asp Leu Pro Tyr Val Glu Val Val Ser Ser Glu Arg
            180                 185                 190 gag atg ata aag aga ttt ctc agg att atc agg gag aag gat cct gac        624
Glu Met Ile Lys Arg Phe Leu Arg Ile Ile Arg Glu Lys Asp Pro Asp
        195                 200                 205 att ata gtt act tat aat gga gac tca ttc gac ttc cca tat tta gcg        672
Ile Ile Val Thr Tyr Asn Gly Asp Ser Phe Asp Phe Pro Tyr Leu Ala
    210                 215                 220 aaa agg gca gaa aaa ctt ggg att aaa tta acc att gga aga gat gga        720
Lys Arg Ala Glu Lys Leu Gly Ile Lys Leu Thr Ile Gly Arg Asp Gly
225                 230                 235                 240 agc gag ccc aag atg cag aga ata ggc gat atg acg gct gta gaa gtc        768
Ser Glu Pro Lys Met Gln Arg Ile Gly Asp Met Thr Ala Val Glu Val
                245                 250                 255 aag gga aga ata cat ttc gac ttg tat cat gta ata aca agg aca ata        816
Lys Gly Arg Ile His Phe Asp Leu Tyr His Val Ile Thr Arg Thr Ile
            260                 265                 270 aat ctc cca aca tac aca cta gag gct gta tat gaa gca att ttt gga        864
Asn Leu Pro Thr Tyr Thr Leu Glu Ala Val Tyr Glu Ala Ile Phe Gly
        275                 280                 285 aag cca aag gag aag gta tac gcc gac gag ata gca aaa gcc tgg gaa        912
Lys Pro Lys Glu Lys Val Tyr Ala Asp Glu Ile Ala Lys Ala Trp Glu
    290                 295                 300 agt gga gag aac ctt gag aga gtt gcc aaa tac tcg atg gaa gat gca        960
Ser Gly Glu Asn Leu Glu Arg Val Ala Lys Tyr Ser Met Glu Asp Ala
305                 310                 315                 320 aag gca act tat gaa ctc ggg aaa gaa ttc ctt cca atg gaa att cag       1008
Lys Ala Thr Tyr Glu Leu Gly Lys Glu Phe Leu Pro Met Glu Ile Gln
                325                 330                 335 ctt tca aga tta gtt gga caa cct tta tgg gat gtt tca agg tca agc       1056
Leu Ser Arg Leu Val Gly Gln Pro Leu Trp Asp Val Ser Arg Ser Ser
            340                 345                 350 aca ggg aac ctt gta gag tgg ttc tta ctt agg aaa gcc tac gaa aga       1104
Thr Gly Asn Leu Val Glu Trp Phe Leu Leu Arg Lys Ala Tyr Glu Arg
        355                 360                 365 aac gaa gta gct cca aac aag cca agt gaa gag gag tcc ggg gat ctg       1152
Asn Glu Val Ala Pro Asn Lys Pro Ser Glu Glu Glu Ser Gly Asp Leu
    370                 375                 380 gac gac ctc agg ctc tcc ttg gag ctc tcc cgg gtg cgc acc gac ctc       1200
Asp Asp Leu Arg Leu Ser Leu Glu Leu Ser Arg Val Arg Thr Asp Leu
385                 390                 395                 400 ccc ctg gag gtg gac ctc gcc cag ggg cgg gag ccc gac cgg gag ggg       1248
Pro Leu Glu Val Asp Leu Ala Gln Gly Arg Glu Pro Asp Arg Glu Gly
                405                 410                 415 ctt agg gcc ttc ctg gag agg ctg gag ttc ggc agc ctc ctc cac gag       1296
Leu Arg Ala Phe Leu Glu Arg Leu Glu Phe Gly Ser Leu Leu His Glu
            420                 425                 430 ttc ggc ctc ctg gag gcc ccc gcc ccc ctg gag gag gcc ccc tgg ccc       1344
Phe Gly Leu Leu Glu Ala Pro Ala Pro Leu Glu Glu Ala Pro Trp Pro
        435                 440                 445 ccg ccg gaa ggg gcc ttc gtg ggc ttc gtc ctc tcc cgc ccc gag ccc       1392
Pro Pro Glu Gly Ala Phe Val Gly Phe Val Leu Ser Arg Pro Glu Pro
    450                 455                 460
```

```
atg tgg gcg gag ctt aaa gcc ctg gcc gcc tgc agg gac ggc cgg gtg      1440
Met Trp Ala Glu Leu Lys Ala Leu Ala Ala Cys Arg Asp Gly Arg Val
465                 470                 475                 480 cac cgg gca gca gac ccc ttg gcg ggg cta aag gac ctc aag gag gtc      1488
His Arg Ala Ala Asp Pro Leu Ala Gly Leu Lys Asp Leu Lys Glu Val
                485                 490                 495 cgg ggc ctc ctc gcc aag gac ctc gcc gtc ttg gcc tcg agg gag ggg      1536
Arg Gly Leu Leu Ala Lys Asp Leu Ala Val Leu Ala Ser Arg Glu Gly
    500                 505                 510 cta gac ctc gtg ccc ggg gac gac ccc atg ctc ctc gcc tac ctc ctg      1584
Leu Asp Leu Val Pro Gly Asp Asp Pro Met Leu Leu Ala Tyr Leu Leu
        515                 520                 525 gac ccc tcc aac acc acc ccc gag ggg gtg gcg cgg cgc tac ggg ggg      1632
Asp Pro Ser Asn Thr Thr Pro Glu Gly Val Ala Arg Arg Tyr Gly Gly
530                 535                 540 gag tgg acg gag gac gcc gcc cac cgg gcc ctc ctc tcg gag agg ctc      1680
Glu Trp Thr Glu Asp Ala Ala His Arg Ala Leu Leu Ser Glu Arg Leu
545                 550                 555                 560 cat cgg aac ctc ctt aag cgc ctc gag ggg gag gag aag ctc ctt tgg      1728
His Arg Asn Leu Leu Lys Arg Leu Glu Gly Glu Glu Lys Leu Leu Trp
                565                 570                 575 ctc tac cac gag gtg gaa aag ccc ctc tcc cgg gtc ctg gcc cac atg      1776
Leu Tyr His Glu Val Glu Lys Pro Leu Ser Arg Val Leu Ala His Met
                580                 585                 590 gag gcc acc ggg gta cgg ctg gac gtg gcc tac ctt cag gcc ctt tcc      1824
Glu Ala Thr Gly Val Arg Leu Asp Val Ala Tyr Leu Gln Ala Leu Ser
            595                 600                 605 ctg gag ctt gcg gag gag atc cgc cgc ctc gag gag gag gtc ttc cgc      1872
Leu Glu Leu Ala Glu Glu Ile Arg Arg Leu Glu Glu Glu Val Phe Arg
610                 615                 620 ttg gcg ggc cac ccc ttc aac ctc aac tcc cgg gac cag ctg gaa agg      1920
Leu Ala Gly His Pro Phe Asn Leu Asn Ser Arg Asp Gln Leu Glu Arg
625                 630                 635                 640 gtg ctc ttt gac gag ctt agg ctt ccc gcc ttg ggg aag acg caa aag      1968
Val Leu Phe Asp Glu Leu Arg Leu Pro Ala Leu Gly Lys Thr Gln Lys
                645                 650                 655 aca ggc aag cgc tcc acc agc gcc gcg gtg ctg gag gcc cta cgg gag      2016
Thr Gly Lys Arg Ser Thr Ser Ala Ala Val Leu Glu Ala Leu Arg Glu
                660                 665                 670 gcc cac ccc atc gtg gag aag atc ctc cag cac cgg gag ctc acc aag      2064
Ala His Pro Ile Val Glu Lys Ile Leu Gln His Arg Glu Leu Thr Lys
            675                 680                 685 ctc aag aac acc tac gtg gac ccc ctc cca agc ctc gtc cac ccg agg      2112
Leu Lys Asn Thr Tyr Val Asp Pro Leu Pro Ser Leu Val His Pro Arg
690                 695                 700 acg ggc cgc ctc cac acc cgc ttc aac cag acg gcc acg gcc acg ggg      2160
Thr Gly Arg Leu His Thr Arg Phe Asn Gln Thr Ala Thr Ala Thr Gly
705                 710                 715                 720 agg ctt agt agc tcc gac ccc aac ctg cag aac atc ccc gtc cgc acc      2208
Arg Leu Ser Ser Ser Asp Pro Asn Leu Gln Asn Ile Pro Val Arg Thr
                725                 730                 735 ccc ttg ggc cag agg atc cgc cgg gcc ttc gtg gcc gag gcg ggt tgg      2256
Pro Leu Gly Gln Arg Ile Arg Arg Ala Phe Val Ala Glu Ala Gly Trp
                740                 745                 750 gcg ttg gtg gcc ctg gac tat agc cag ata gag ctc cgc gtc ctc gcc      2304
Ala Leu Val Ala Leu Asp Tyr Ser Gln Ile Glu Leu Arg Val Leu Ala
            755                 760                 765 cac ctc tcc ggg gac gaa aac ctg atc agg gtc ttc cag gag ggg aag      2352
His Leu Ser Gly Asp Glu Asn Leu Ile Arg Val Phe Gln Glu Gly Lys
        770                 775                 780
```

```
gac atc cac acc cag acc gca agc tgg atg ttc ggc gtc ccc ccg gag      2400
Asp Ile His Thr Gln Thr Ala Ser Trp Met Phe Gly Val Pro Pro Glu
785                 790                 795                 800 gcc gtg gac ccc ctg atg cgc cgg gcg gcc aag acg gtg aac ttc ggc      2448
Ala Val Asp Pro Leu Met Arg Arg Ala Ala Lys Thr Val Asn Phe Gly
            805                 810                 815 gtc ctc tac ggc atg tcc gcc cat agg ctc tcc cag gag ctt gcc atc      2496
Val Leu Tyr Gly Met Ser Ala His Arg Leu Ser Gln Glu Leu Ala Ile
        820                 825                 830 ccc tac gag gag gcg gtg gcc ttt ata gag cgc tac ttc caa agc ttc      2544
Pro Tyr Glu Glu Ala Val Ala Phe Ile Glu Arg Tyr Phe Gln Ser Phe
835                 840                 845 ccc aag gtg cgg gcc tgg ata gaa aag acc ctg gag gag ggg agg aag      2592
Pro Lys Val Arg Ala Trp Ile Glu Lys Thr Leu Glu Glu Gly Arg Lys
    850                 855                 860 cgg ggc tac gtg gaa acc ctc ttc gga aga agg cgc tac gtg ccc gac      2640
Arg Gly Tyr Val Glu Thr Leu Phe Gly Arg Arg Arg Tyr Val Pro Asp
865                 870                 875                 880 ctc aac gcc cgg gtg aag agc gtc agg gag gcc gcg gag cgc atg gcc      2688
Leu Asn Ala Arg Val Lys Ser Val Arg Glu Ala Ala Glu Arg Met Ala
            885                 890                 895 ttc aac atg ccc gtc cag ggc acc gcc gcc gac ctc atg aag ctc gcc      2736
Phe Asn Met Pro Val Gln Gly Thr Ala Ala Asp Leu Met Lys Leu Ala
        900                 905                 910 atg gtg aag ctc ttc ccc cgc ctc cgg gag atg ggg gcc cgc atg ctc      2784
Met Val Lys Leu Phe Pro Arg Leu Arg Glu Met Gly Ala Arg Met Leu
    915                 920                 925 ctc cag gtc cac gac gag ctc ctc ctg gag gcc ccc caa gcg cgg gcc      2832
Leu Gln Val His Asp Glu Leu Leu Leu Glu Ala Pro Gln Ala Arg Ala
930                 935                 940 gag gag gtg gcg gct ttg gcc aag gag gcc atg gag aag gcc tat ccc      2880
Glu Glu Val Ala Ala Leu Ala Lys Glu Ala Met Glu Lys Ala Tyr Pro
945                 950                 955                 960 ctc gcc gtg ccc ctg gag gtg gag gtg ggg atg ggg gag gac tgg ctt      2928
Leu Ala Val Pro Leu Glu Val Glu Val Gly Met Gly Glu Asp Trp Leu
            965                 970                 975 tcc gcc aag ggt tag                                                  2943
Ser Ala Lys Gly
            980

<210> SEQ ID NO 5

<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE   : 5 aaacccggga tgtggattac ataactgaag aa                                    32

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 6
aaaaagtact cctcttcact tg                                               22
```

```
<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 7
agatctggac gatctgaagc tctcctggga c                           31

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 8
gtcgactatc actccttggc ggagagcca                              29

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
gatgagttcg tgtccgtaca actgg                                  25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
ggttatcgaa atcagccaca gcgcc                                  25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
tcgatcacac tcagcaactg cgtgg                                  25

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 12
agatctggac gacctcaggc tctccttgga g                           31

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer
```

```
<400> SEQUENCE: 13
gtcgacctaa cccttggcgg aaagcca                                27

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 14
ttcccagcca cacgctgcat gacat                                  25

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 15
tgttgacctt gcctgcagca acgc                                   24
```